United States Patent
Slanetz

(10) Patent No.: US 11,723,921 B2
(45) Date of Patent: Aug. 15, 2023

(54) MODULATED IMMUNODOMINANCE THERAPY

(71) Applicant: Geneius Biotechnology, Inc., Natick, MA (US)

(72) Inventor: Alfred E. Slanetz, Cohasset, MA (US)

(73) Assignee: GENEIUS BIOTECHNOLOGY, INC., Natick, MA (US)

( * ) Notice: Subject to any disclaimer, the term of this patent is extended or adjusted under 35 U.S.C. 154(b) by 449 days.

(21) Appl. No.: 15/486,864

(22) Filed: Apr. 13, 2017

(65) Prior Publication Data

US 2017/0216357 A1 Aug. 3, 2017

Related U.S. Application Data

(63) Continuation of application No. 14/122,036, filed as application No. PCT/US2012/039605 on May 25, 2012, now abandoned.

(60) Provisional application No. 61/490,505, filed on May 26, 2011.

(51) Int. Cl.

| A61K 35/17 | (2015.01) |
|---|---|
| A61K 39/00 | (2006.01) |
| A61K 39/29 | (2006.01) |
| A61K 39/12 | (2006.01) |
| A61K 39/245 | (2006.01) |
| C12N 7/00 | (2006.01) |
| A61K 9/00 | (2006.01) |
| C12N 5/0783 | (2010.01) |
| A61K 35/12 | (2015.01) |

(52) U.S. Cl.
CPC ............ *A61K 35/17* (2013.01); *A61K 9/0019* (2013.01); *A61K 9/0021* (2013.01); *A61K 39/0008* (2013.01); *A61K 39/0011* (2013.01); *A61K 39/12* (2013.01); *A61K 39/245* (2013.01); *A61K 39/292* (2013.01); *C12N 5/0636* (2013.01); *C12N 7/00* (2013.01); *A61K 2035/124* (2013.01); *A61K 2039/5158* (2013.01); *A61K 2039/53* (2013.01); *A61K 2039/55566* (2013.01); *A61K 2039/585* (2013.01); *C12N 2501/2302* (2013.01); *C12N 2501/2304* (2013.01); *C12N 2501/2306* (2013.01); *C12N 2501/2307* (2013.01); *C12N 2501/2312* (2013.01); *C12N 2501/2315* (2013.01); *C12N 2501/2321* (2013.01); *C12N 2501/999* (2013.01); *C12N 2710/16034* (2013.01); *C12N 2710/16234* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| 2004/0023377 A1 | 2/2004 | Assenmacher et al. |
| 2004/0072240 A1 | 4/2004 | Kosmatopoulos et al. |

FOREIGN PATENT DOCUMENTS

| WO | 97/33602 A1 | 9/1997 |
| WO | 98/33888 A1 | 8/1998 |
| WO | 2004/042041 A1 | 5/2004 |
| WO | 2011/028531 A1 | 3/2011 |

OTHER PUBLICATIONS

Bollard et al. (Blood, 2007, 2838-2845). (Year: 2007).*
Redchenko et al. (Journal of Virology, 1999, p. 334-342). (Year: 1999).*
Le et al. (Cancer Immunol Immunother (2009) 58:1565-1576). (Year: 2009).*
Melchionda et al. (J Clin Invest. 2005; 115(5):1177-1187). (Year: 2005).*
Wolfl et al.(Cancer Immunol Immunother (2011) 60:173-186). (Year: 2011).*
Liu et al. (J Immunol 2006; 177:712-721). (Year: 2006).*
Feltkamp, M. C.W., et al.,"Cytotoxic T Lymphocytes Raised Against a Subdominant Epitope Offered as a Synthetic Peptide Eradicate Human Papillomavirus Type 16 Induced Tumors"; European Journal of Immunology (1995), vol. 25, pp. 2638-2642.

(Continued)

*Primary Examiner* — Zachary S Skelding
(74) *Attorney, Agent, or Firm* — Perkins Coie LLP; Michael Wise; Allison M. Glasunow

(57) ABSTRACT

The invention involves generating a T cell response to subdominant antigens and using the cells to therapeutically change the cellular homeostasis and nature of the immune response. In a preferred embodiment, the cells are generated outside of the patient avoiding the influence of the patient's immunologic milieu. By stimulating and growing the T cells from a patient in a tissue culture to one or more subdominant antigens and the transplanting them into the patient, if enough cells are expanded and transplanted, the transplanted cells overwhelm the endogenous dominant T cells in the response to either break or induce immune tolerance or otherwise modify the immune response to the cells or organism expressing that antigen. When the memory cells are established they are then reflective of this new immunodominance hierarchy so that the desired therapeutic effect is long lasting. In effect, the transplantation exogenously generated T cells reactive to the subdominant antigens is recapitulating priming and rebalancing the patient's immune response to target previously subdominant antigens in the cells or organism to produce a therapeutic benefit.

12 Claims, 15 Drawing Sheets

Specification includes a Sequence Listing.

(56) References Cited

OTHER PUBLICATIONS

Eberl, G. et al., "Immunodominance of Cytotoxic T Lymphocyte Epitopes Co-injected in vivo and Modulation by Interleukin-12"; European Journal of Immunology (1996), vol. 26; pp. 2709-2716.

Gottschalk, S. et al., "Generating CTLs against the subdominant Epstein-Barr virus LMP1 antigen for the adoptive immunotherapy of EBV-associated malignancies"; Blood (2003); vol. 101:5; pp. 1905-1912.

Hasan, A. et al., "A Panel of Artificial APCs Expressing Prevalent HLA Alleles Permits Generation of Cytotoxic T cells Specific for Both Dominant and Dubdominant Viral Epitopes for Adoptive Therapy"; Journal of Immunology (2009); vol. 183:4; pp. 2837-2850.

Rodriguez-Pinto, et al., "B cells can prime naive CD4+ T cells in vivo in the absence of other professional antigen-presenting cells in a CD154-CD40-dependent manner"; European J. Immunol. (2005); vol. 35; pp. 1097-1105.

Subklewe, M. et al., "Dendritic cells expand Epstein Barr virus specific CD8+ T cell responses more efficiently than EBV transformed B cells" Human Immunology (2005); vol. 66:9; pp. 938-949.

Duraiswamy, J et al., "Induction of Therapeutic T-Cell Responses to Subdominant Tumor-associated Viral Oncogene after Immunization with Replication-incompetent Polyepitope Adenovirus Vaccine"; Cancer Research (2004); vol. 64; pp. 1483-1489.

Duraiswamy, J. et al., "Therapeutic LMP1 Polyepitope Vaccine for EBV-associated Hodgkin Fisease and Nasopharyngeal Carcinoma"; Blood (2003); vol. 101:8; pp. 3150-3156.

Tsai, V. et al., "Identification of Subdominant CTL Epitopes of the GP100 Melanoma-Associated Tumor Antigen by Primary in vitro Immunization with Peptide-Pulsed Dendritic Cells"; J. Immunol (1997); vol. 158:4; pp. 1796-1802.

Schirmbeck, R. et al., The Immunogenicity of Adenovirus Vectors Limits the Multispecificity of CD8 T-cell Responses to Vector-encoded Transgenic Antigens; Molecular Therapy (2008); vol. 16:9; pp. 1609-1616.

Long, S. A, et al., "Combination of Rapamycin and IL-2 Increases De Novo Induction of Human CD4+CD25+FOXP3+ T Cells," J. Autoimmun. (2008) 30(4):293-302.

Rochman, Y., et al., "New Insights into the Regulation of T Cells by Gamma(c) Family Cytokines," Nat. Rev. Immunol. (2009) 9(7):480-90.

* cited by examiner

Before

6 Mo. Post T Cell Therapy

Normal

Immunized with human proteoglycan

Treated with T cells

MODULATED IMMUNODOMINANCE THERAPY

CROSS-REFERENCE TO RELATED APPLICATIONS

This application is a continuation of U.S. patent application Ser. No. 14/122,036, filed Nov. 25, 2013, now published as United States Patent Publication 2014-0099341, which is a national stage application, filed under 35 U.S.C § 371, of International Application No. PCT/US2012/039605, filed May 25, 2012, which related to provisional application U.S. Ser. No. 61/490,505, filed May 26, 2011, the contents which are hereby incorporated by reference in its entirety.

SEQUENCE LISTING

This application contains a Sequence Listing, which has been filed electronically in ASCII format and is hereby incorporated by reference in its entirety. Said ASCII copy, created on Jul. 28, 2020, is named 170331-46307_ST25.txt and is 3,299 bytes in size.

BACKGROUND OF THE INVENTION

The present invention relates to a novel therapeutic for cancer, chronic infections, autoimmune diseases, and transplantation based upon the modification of the immunodominance hierarch by therapeutic manipulation of cellular homeostasis.

The clinical management of cancer is specific for each site of origin and, for the most part, depends upon stage of the disease (i.e., how far the tumor has invaded locally or spread to other organs by metastasis). Surgery and/or localized radiotherapy are generally the treatment of choice for the primary tumor with chemotherapy, monoclonal antibody or cytokine therapy or whole body irradiation being treatment for metastatic disease. Recently, the first dendritic cell therapy, Provenge, was approved for Prostate cancer with a 4-month progression benefit. Diagnosis is still based upon histologic analysis of the biopsy. Molecular markers are sometimes standard if they will be helpful in the selection of a drug (e.g., Herceptin). However, creating a profile of the immune response has not been done on a routine clinical basis.

The environment in which a T cell sees an antigen during the primary immune response determines the nature of subsequent recall response. The initial recognition event and microenvironment around that primary cell can result in many outcomes. If the antigen is presented by a nonprofessional APC, only a subset of the epitopes may be released during processing. If a costimulatory signal such as CD28 or TNF is missing, the T cells may be anergized. Depending on the microenvironment, the T cell may differentiate into a regulatory T cell, a T helper cell secreting Th1 cytokine (driving more of a cellular immune response with proliferation of $CD8^+$ CTL effectors) or a T helper cell secreting Th2 cytokine (driving more of a humoral immune response with proliferation and maturation of B cells and antibody production). In addition, the immune response will evolve such that T cells responding to certain epitopes of an antigen or certain antigens in the milieu will grow at the expense of T cells in the population which are reactive with other epitopes or antigens in the milieu. Because of exponential cell growth, as the primary immune response subsides, the ratio of these T cells is further accentuated and stored in the form of memory such that upon secondary stimulation, the immune response within that individual is focused on a small subset of the possible epitopes. While there are multiple mechanisms at work, as an operative model, the T cells that grow out to dominate the population are those responding to the epitopes or antigens which come to dominate the immune response. In the primary immune response, they are growing out at the expense of the T cells responding to subdominant epitopes and, due to memory, dominate subsequent immune responses.

Over a period of days after a person's immune system first sees an antigen, a dominant population of T cells responding to a limited number of dominant epitopes is generated and these T cells determine the nature of the response to that antigen thereafter. While there are multiple types of cells involved, the working model associated with this invention is that if the T cells responding to the dominant epitope on the dominant antigens grow out as responsive T cells (e.g. $CD4^+$:TH1, TH2, Treg, T follicular helper, TH17, TH22, TH9; $CD8^+$ CTL's), a cellular or humoral immune response results. However, if the T cells in the dominant population are suppressive T cells (e.g., Treg, TH17, anergized T cells), tolerance is induced. T cells responding to subdominant antigens are overwhelmed by the clonal population of T cells responding to the dominant antigens.

In the case of cancer, chronic or latent infections, the local antigen processing/presenting and costimulatory environment impacts the primary immune response to the dominant antigens such that the T cell response to the dominant antigens in the tumor or infectious agent is balanced towards tolerance or ineffective response rather than a potent effector response. Due to differences in antigen processing and costimulation (CD28 and cytokines), this could be accentuated in organs where dendritic cells (DCs) are not the prevalent antigen presenting cells (APCs) unlike the body surfaces where DC are the predominant antigen presenting cell. It is also well known that tumors and infectious agents create an immunosuppressive environment which is not optimal for a strong primary immune response. Alternatively, if a dominant antigen results in cells which are reacting to self, tolerance is broken and autoimmunity ensues. Such tolerance could be broken by the presence of a chronic or latent virus leading to a response (even chronically to weak subdominant antigens). There are multiple associations of viruses with autoimmunity. The inflammation at the site leads to release of other antigens while the viral antigens provide help to the T cells responsive to the organ, causing autoimmunity. After the dominance hierarchy is established in the primary response and reinforced by memory, the immune system in the patient will effectively replicate the same response each time the antigen is present.

An ongoing immune response against a dominant epitope can diminish the response to a subdominant epitope (Wolpert E Z 1998, Kedl R M 2003). The dominance/subdominance hierarchy can be somewhat fluid. For instance, deleting or silencing T cell responses against a dominant epitope can lead to the appearance of a previously undetectable response against subdominant epitopes (Van derMost R G et al. 1997, Andreansky S S et al. 2005). Similarly, removal of a dominant sequence in an epitope does not eliminate the response to the antigen but rather results in the host responding more strongly to a previously subdominant epitope (Allan J E and Doherty P C 1985, Mylin L M et al. 2000).

SUMMARY OF THE INVENTION

The present invention relates to a novel therapeutic for cancer, chronic infections, autoimmune diseases, and transplantation based upon the modification of the immunodominance hierarch by therapeutic manipulation of cellular homeostasis.

Disclosed is a novel approach to rebalance the immune response to antigens to provide significant therapeutic benefit in, among others, cancer, chronic and latent infection, autoimmunity and transplantation. By generating immune responses to subdominant epitopes and subdominant antigens in a controlled microenvironment, the invention fundamentally changes the nature of the immune response to the disease to one that provides therapeutic benefit. It can change the balance of the immune response before or after a prior immune response has occurred to the antigen or even if there is one ongoing.

The present invention features a method comprising identifying a dominant antigen or epitope and a subdominant antigen or epitope in a patient sample, cultivating a T cell capable of recognizing the subdominant antigen or epitope, and treating a patient with an effective number of the T cells to alter the immunodominance hierarchy of the patient.

The present invention also features methods for altering the immunodominance hierarchy of a patient comprising identifying at least one subdominant antigen or epitope in a patient sample, cultivating a T cell capable of recognizing the subdominant antigen or epitope, and treating the patient with an effective number of those T cells to provide therapeutic benefit.

In some aspects, the invention further comprises cultivating a T cell in the absence of a dominant antigen or epitope. In other aspects, the invention further comprises cultivating a T cell in the absence or presence of agents that enrich suppressive T cells or responsive T cells. Such agents can include, but are not limited to, growth factors, hormones, or other immune cells.

In some aspects, the invention further comprises administering the effective number of T cells via intradermal administration.

In other aspects, the invention further comprises pre-treating the patient with a conditioning agent to reduce the number of endogenous T cells prior to treating the patient with the cultivated T cells. The conditioning agent can be, but is not limited to, a chemotherapeutic agent.

In some aspects, the T cell is provided ex vivo from a patient.

The subdominant antigen or subdominant epitope is, for example, an antigen or epitope to which a cellular or humoral immune response is not detectable or is only detectable at a low level. Alternatively, the subdominant antigen or subdominant epitope is an antigen or epitope that evokes a weaker tolerance or immune response than that of a dominant antigen or dominant epitope. The subdominant antigen is, for example, a viral antigen, a fungal antigen, a bacterial antigen, a parasitic antigen, a prion antigen, a tumor antigen, or an antigen associated with autoimmunity, allergy, inflammation, organ transplant rejection, or graft versus host disease. The viral antigen is, for example, a chronic or latent viral antigen. The viral antigen is be from EBV, HPV, HSV, VZV, Hepatitis B, Hepatitis C, HW, HTLV, CMV, RSV, or influenza. The tumor antigen is, for example, a tumor-associated antigen, a tumor specific antigen, or an antigen associated with cancer stem cells or metastasis.

The present invention also features methods for identifying a dominant antigen or epitope and/or a subdominant antigen or epitope in a patient sample, cultivating a T cell capable of recognizing the subdominant antigen or epitope, wherein the T cell is a suppressive T cell, and treating a patient with an effective number of said T cell to alter the immunodominance hierarchy of the patient, thereby inducing tolerance in the patient for treatment or prevention of an autoimmune disease, allergy, inflammation, organ transplantation rejection, or graft versus host disease.

The present invention also features methods for identifying a dominant antigen or epitope and/or a subdominant antigen or epitope in a patient sample, cultivating a T cell capable of recognizing the subdominant antigen or epitope, wherein the T cell is a responsive T cell, and treating a patient with an effective number of said T cell to alter the immunodominance hierarchy of the patient, thereby inducing a cytotoxic immune response in the patient for treatment or prevention of an infection or cancer. The infection is, for example, a bacterial, viral, parasitic, or prion infection.

In any of the methods of the present invention, treatment or prevention of a disease, infection, cancer, or medical condition includes alleviating or ameliorating at least one symptom of a disease, infection, cancer, or medical condition. Therapeutic benefit includes any alleviation, amelioration, improvement, prevention, or treatment of at least one symptom of a disease, infection, cancer, or medical condition.

In some aspects, the patient sample is a blood sample.

The present invention also features a method further comprising re-profiling of the patient by assaying for a tolerance or humoral or cellular immune response in response to the subdominant antigen or epitope to determine if the therapy successfully rebalanced the immune response.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION

A. Definitions

Figure 1A:
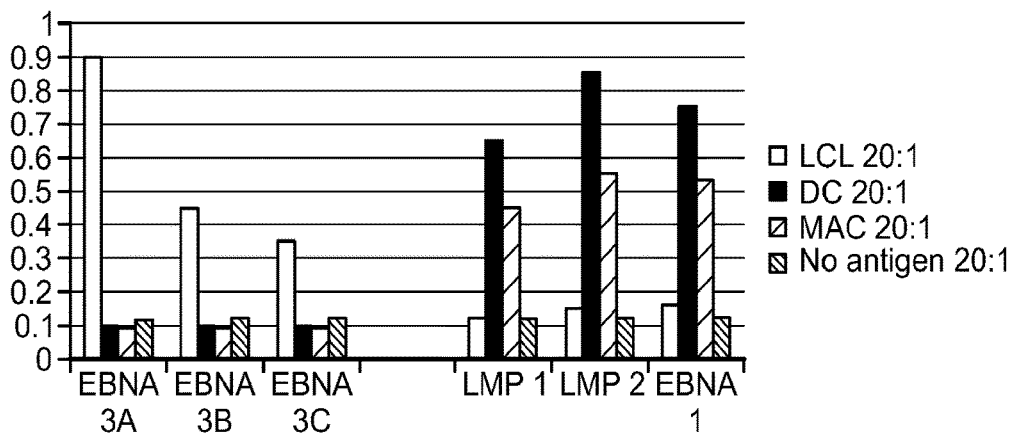
FIGS. 1A, 1B and 1C show the results of a $^{51}$Cr release assay.

The term "antibody" is used in the broadest sense and specifically covers human, non-human (e.g., murine) and humanized monoclonal antibodies (including full length monoclonal antibodies), polyclonal antibodies, multi-specific antibodies (e.g., bispecific antibodies), and antibody fragments so long as they exhibit the desired biological activity.

The term "antigen," refers to a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes.

"Antigen presenting cells" or "APCs" are cells of the immune system used for presenting antigen to T cells. APCs include dendritic cells, monocytes, macrophages, marginal zone Kupffer cells, microglia, Langerhans cells, T cells, and B cells (see, e.g., Rodriguez-Pinto and Moreno (2005) Eur. J. Immunol. 35:1097-1105).

"Autoimmunity," "autoimmune disease," "autoimmune condition" or "autoimmune disorder" refers to a set of sustained organ-specific or systemic clinical symptoms and signs associated with altered immune homeostasis that is manifested by qualitative and/or quantitative defects of expressed autoimmune repertoires. Autoimmune disease pathology is manifested as a result of either structural or functional damage induced by the autoimmune response. Autoimmune diseases are characterized by humoral (e.g., antibody-mediated), cellular (e.g., cytotoxic T lymphocyte-mediated), or a combination of both types of immune responses to epitopes on self-antigens. The immune system of the affected individual activates inflammatory cascades aimed at cells and tissues presenting those specific self-antigens. The destruction of the antigen, tissue, cell type or organ attacked gives rise to the symptoms of the disease.

The term "cancer" refers to a disease or disorder that is characterized by unregulated cell growth. Examples of cancer include, but are not limited to, carcinoma, lymphoma, blastoma and sarcoma. Examples of specific cancers include, but are not limited to, lung cancer, colon cancer, breast cancer, testicular cancer, stomach cancer, pancreatic cancer, ovarian cancer, liver cancer, bladder cancer, colorectal cancer, and prostate cancer. Additional cancers known to those of skill in the art are also contemplated.

"Dominant antigen" or "dominant epitope" refers to an antigen or epitope that evokes a strong tolerance or immune response, which may be characterized by the presence of T cells specific for that antigen or epitope in an amount greater than about 70% of the total number of responding T cells.

The term "epitope" refers to a set of amino acid residues that is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor or HLA molecule.

"Hepatitis" refers to a medical condition defined by the inflammation of the liver.

"Human Leukocyte Antigen" or "HLA" is a human class I or class II Major Histocompatibility Complex (MHC) protein (see, e.g., Stites, et al., IMMUNOLOGY, 8TH ED., Lange Publishing, Los Altos, Calif. (1994).

An "immune response" refers to a response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunodominance is the observation that in spite of a large number of possible epitopes (antigen fragments) in an antigen, the immune system focuses its response on a limited number of epitopes and can be ordered as a reproducible hierarchy (Sercarz et al. 1993). Immunodominance holds true for immune responses to artificial antigens, human viruses including influenza and vaccinia, and intracellular bacteria (Chen W S 1994, Belze G T et al. 2000, Chen W 2000, Tscharke D C 2005). The final outcome of immunodominance is determined by a number of steps, including MHC binding affinity, efficiency of cellular processing to generate appropriate MHC binding peptides, availability of TCRs to recognize complexes between the MHC binding peptides, and MHC followed by cellular immunoregulatory mechanisms (Yewdell J W 2006, Sette A et al. 2009).

"Lymphocytes" refers to a type of white book cell that is involved in the immune defenses of the body. There are two main types of lymphocytes: B cells and T cells.

"Major Histocompatibility Complex" or "MHC" is a generic designation meant to encompass the histocompatibility antigen systems described in different species, including the human leukocyte antigens ("HLA").

"Subdominant antigen" or "subdominant epitope" refers to an antigen or epitope that evokes a weaker tolerance or immune response than that of a dominant antigen or dominant epitope.

The term "treatment" refers to a clinical intervention made in response to a disease, disorder or physiological condition manifested by a patient or to be prevented in a patient. The aim of treatment includes the alleviation and/or prevention of symptoms, as well as slowing, stopping or reversing the progression of a disease, disorder, or condition. 'Treatment" refers to both therapeutic treatment and prophylactic or preventative measures. Those in need of treatment include those already affected by a disease or disorder or undesired physiological condition as well as those in which the disease or disorder or undesired physiological condition is to be prevented.

"Tumor" refers to all neoplastic cell growth and proliferation, whether malignant or benign, and all pre-cancerous and cancerous cells and tissues.

"____-mer" refers to a linear sequence of ____ amino acids that occur in a target antigen.

B. Assays that Recognize/Distinguish the Subdominant Epitope from the Dominant One The patient's tumor or infection is first assayed for the presence of a panel of tumor associated, viral or other antigens. This is generally done by immunohistochemistry on the tumor biopsy or FACS in the case of hematologic malignancies. The patient's tumor or infection is assayed for the presence of a panel of tumor associated, viral or other antigens. This is generally done by immunohistochemistry on the tumor biopsy or FACS in the case of hematologic malignancies. The patient's blood is drawn and tested for both humoral and cellular immune response to the antigens which are present. The antigens to which the immune response is not detectable or detectable at a low level are proactively selected to grow T cells in vitro. After these T cells are grown, they can be tested for response to the antigens re-infused, and the patient's blood can be assayed for the response to the antigens. In this way, the patient's immune response can be effectively rebalanced to provide therapeutic benefit. In a preferred embodiment, the assays of humoral immunity can include but is not limited to an ELISA assay. In a preferred embodiment, the assay of cellular immunity can include but is not limited to Intracellular cytokine staining for cytokines (ICS), including but not limited to Interferon γ (IFNγ) and Tumor necrosis Factor α (TNFα). The subsets of T cells responding (e.g., CD8, CD4, Treg) can also be assayed in this assay. Alternatively, the assay of cellular immunity can include but is not limited to ELISPOT assay for IFNγ or TNFα. In an alternative embodiment, the Elispot or ICS can assay for IL-4, IL-12 (TH2 and TH1), IL-10 (Treg) or IL-21 (T follicular helper cell subset). In still another embodiment, the cellular immune profiling assay can be Intracellular Staining (ICS) for these or other cytokines. The antigens tested can be full antigens, antigens with epitopes deleted or dominant or subdominant epitopes. In the case of epitopes, bioinformatics software can be used to predict epitopes which would bind to the patients MHC and these epitopes are then assayed. In one embodiment, this software is the Net MHC-pan or the consensus epitope immunoinformatics software described in the assay section. In the case of epitopes, tetramer binding can be used as an alternative assay to quantify the CTL providing one knows the HLA type. Tetramers including the peptides are combined with the cells and cells stained and FACS used to determine the % of cells recognizing each tetramer. This is useful if the patient is of a known HLA type such as HLA A2. However, the preferred method is the ELISA for humoral response and ICS or Elispot for the cellular response. In a preferred embodiment, the CTL's are generated from peripheral blood. Alternatively, the CTL's are generated from the tumor infiltrating lymphocytes (TIL) or from the DTH surrounding the injection site.

DTH infiltrating lymphocytes can be prepared by taking a 4 mm punch biopsy from the skin minced in RPMI medium 1640 with 10% FCS (CSL). Single cell suspensions were stimulated with 1 µg/ml phytohemagglutinin (Sigma) and cocultured with irradiated autologous PBMC'S with 10 IU/ml IL-2 (Cetus) and 10 ng/ml IL-7 (Peprotech, Rocky Hill, N.J.). Medium was replenished each 2-3 days.

For humoral immune response profiling, serum from the patient is serially diluted 1:4 from 1/100 to 1/100000 and used in a standard ELISA with purified recombinant tumor antigens (generally made in $E.\ coli$). From 2 to 10000+ antigens can be assayed. One microgram of each purified protein is absorbed to microwell plates (Nunc) overnight at 4 degrees C. Plates are washed with PBS and blocked with 2% FCS/PBS. Patient serum is diluted in 2% FCS/PBS and added for 2 hours. Plates are washed and goat anti-human IgG-AP (Southern Biotechnology Assoc) is added. Plates are washed, incubated with Attophose substrate (JBL Bioscientific) for 25 min, and immediately read (CytoFluor 2350, Millipore). Readout is UV Absorbance.

There are two methods for cellular response profiling. The first method involves the Enzyme-linked immunosorbent spot ("ELISPOT") assay for IFNγ. Ninety-six well polyvinylidene diflouride backed plates (Millipore, Bedford, Mass.) are coated with 5-15 µg/ml of anti-IFNγ monoclonal antibody 1-DIK (MABTECH, Stockholm, Sweden) at 4 degrees C. overnight. The wells are washed and blocked with 5% human AB serum (Valeant Pharm). $5\times10^6$ PBMCs (or $5\times10^5$ CTL's when the assay is performed post in vitro expansion) are added per well with peptide mixes 2 µM each from each of the antigens. Incubate overnight (18 hours) at 37 degrees C. 5% $CO_2$. Cells are discarded and the wells are washed with PBS containing 0.05% Tween 20. 1 µg/ml biotinylated anti-IFNγ monoclonal antibody 7-B6-1 (MABTECH) is incubated for 2-4 hours at room temperature followed by streptavidin conjugated alkaline phosphatase (MABTECH or Sigma Aldrich) for 2 more hours. This is followed by a 30 minute reaction with 5-bromo-4-chloro-3-indolyl phosphate and nitro blue tetrazolium from the alk-phos substrate kit (Bio-Rad Richmond, Calif.). The spots are to be counted using a dissection microscope (SZ CTV Olympus microscope). Spots can also be counted on an AIDELISPOT reader (Autoimmun Diagnostika, Strassberg, Germany). Each spot is a cell reported as spot forming cells (SFC)/$10^5$ PBMC's. 10 µg/ml PHA can be used as a positive control; cells alone without peptide can serve as the negative control.

The second method involves intracellular cytokine staining for IFNγ and TNFα. $5\times10^6$ PBMC's (or $5\times10^5$ CTL's when the assay is performed post in vitro expansion) are plated in 100 µl PBS 1% FCS 96 well plates together with the peptides ($10^{-5}$ to $10^{-9}$ M final concentration) for each of the epitopes or antigens being studied. After 6 hours of incubation in the presence of IL-2 (150 U/Ml), 50 µM β mercaptoethanol and brefeldin A (1 µg/ml) or Golgi Plug (BD Biosciences, San Diego, Calif.) (both of the latter components to increase accumulation of IFNγ or TNFα in responding cells), cells are pelleted, washed in 200 ml PBS 1% FCS and then labeled with stain for surface antigens (CD4 fluorescein isothiocyanate and CD8 allophycocyanin 0.25 µg/ml (Pharmingen, Becton Dickinson) for 30 minutes at 4 degrees C. (for 30 min on ice). After a wash, cells are permeabilized with Cytofix/Cytoperm for 20 min on ice and then stained with a phycoerythrin conjugated anti-IFNγ (0.4 µg/ml) or anti-TNFα (0.8 µg/ml) antibody (Pharmingen, Becton Dickinson). The cells are then washed, fixed and resuspended in PBS 1% FCS and tested on a FACScan flow cytometer and analyzed using Cell Quest software. Alternatively, FACS Canto (Becton Dickinson) can be used. Other cytokines, including but not limited to IL-12 and IL-4, can be assayed to measure TH1 or TH2 subsets. Cytokine panel to give a broader assay of T cells could measure IL-12, IFN g, IL-4, IL-10 and IL-17. T follicular helper cells can be measured as $CD4^+$, $CXCR5^+$, $ICOS^+$ cells. B cells can be measured as $CD19^+$ and $B220^+$ cells. IL-21 in the T cells should be associated with B cell activation and affinity maturation of antibodies so this could be used to study this as well. As an alternative for profiling IFNγ, IL-4 (BD Biosciences) IL-12, IL-10, IL-17 (R&D Systems), and IL-21 antibody (R&D systems), ELISPOT can also be used. ICS actually profiles the % of CD8 or CD4 T cells responding to different antigens or epitopes. Other cell subsets can be analyzed as well including Treg. A cytochrome labeled CD25 monoclonal antibody can be used as a surface marker of most Tregs. Alternatively, cytochrome labeled Human FoxP3 monoclonal antibody clone 259D/C7 from BD Biosciences is used to stain the cells post permeabilization to measure % Treg cells and their status. IL-10 can also be assayed.

NetMHCpan is a bioinformatics method for quantitative predictions of peptide binding to HLA-A and -B (Nielsen M 2007). A consensus epitope prediction approach has also been developed (Mouaftsi M 2006). These methods can be used to sort all of the potential MHC I epitopes for an antigen and rank the top 1% of peptides and thus predict epitopes. These predicted epitopes would then be synthesized as 9-10 mer peptides and tested (e.g., to patient PBMCs or in a transgenic mouse for the HLA type of interest).

Tetramers with specific MHC (e.g., HLA A A2) are synthesized together with 8 mer peptide epitopes (in the case of class I MHC and 15 mer peptide epitopes in the case of MHC Class II. The cultured T cells are stained with the tetramer diluted 1/200 at room temperature for 20 min; anti CD8 antibody was then added and stained for a further 30 minutes. Cells were then washed and 100,000 acquired on FACS Calibur (BD Biosciences) and analyzed with Flowjo software (Tree Star).

Following therapy, the patient is re-profiled by assaying for a tolerance or humoral or cellular immune response in response to the subdominant antigen or epitope to determine if the therapy successfully rebalanced the immune response.

C. Rebalancing the Immune Response

In one embodiment of the present invention, the immune response can be rebalanced by growing T cells from a patient ex vivo to a subdominant antigen or subdominant epitopes on an antigen followed by infusion or administration of these T cells into the patient. T cells to subdominant antigens or epitopes are grown in tissue culture, ex vivo (away from the patient's immunoregulatory milieu). After growing enough cells to overwhelm the previously dominant cells, the cells are re-infused into the patient to skew the cellular balance and therapeutically switch the dominance hierarchy. In a further preferred embodiment, this number of T cells introduced de novo as therapy is greater than 5% of the T cells responding to the antigen, infectious agent, tumor or organ. The ratio can be further skewed to favor the infused cells by pretreatment of the patient with conditioning agents which reduce the number of endogenous T cells (i.e., chemotherapy).

The present invention involves methods to optimize the growth of T cells to subdominant antigens in tissue culture. In one embodiment, the cells are grown in the absence of dominant antigens. This is accomplished by selection of a professional antigen presenting cell which has not been exposed to dominant antigen and the modification of the antigens to eliminate dominant epitopes or other components which limit the ability of an antigen to be processed.

As the therapeutic method requires T cells to be enriched for and ideally fully responsive to subdominant antigens/epitopes, efficient methods for the growth of such T cells are important. The growth of other T cells to dominant epitopes and antigens increases the time in culture required to generate enough specific cells to skew this ratio. Moreover, the cells growing out to dominant epitopes is working against the achievement of the proper ratio upon reinfusion. Therefore, T cell culture methods which specifically limit the introduction of dominant antigens or epitopes have been developed. For example, while the method is broadly applicable to all tumors, it has distinct advantages for EBV malignancies because it does not use EBV transformed B cells (which express the EBV dominant antigens/epitopes). It is also more reliable when administered to cells in which a significant % of the CTL's are responding to subdominant antigens/epitopes.

Figure 3A:
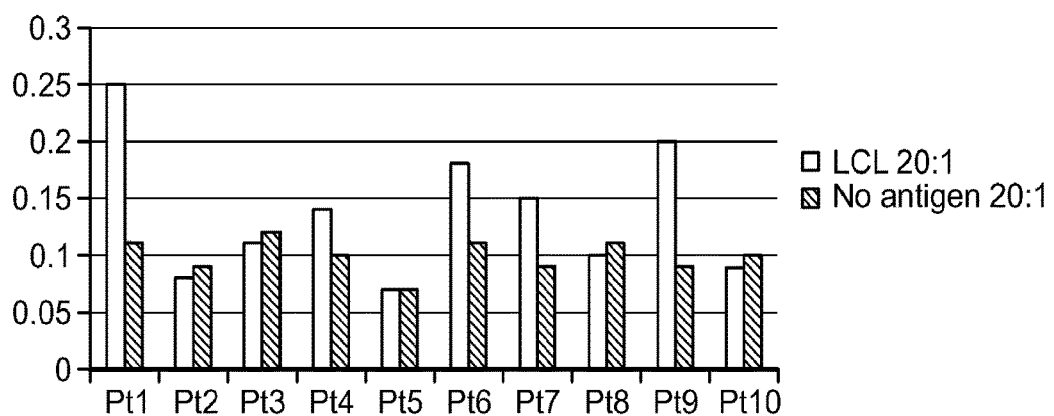
FIGS. 3A and 3B show the results of a $^{51}$Cr release assay.
Figure 3B:
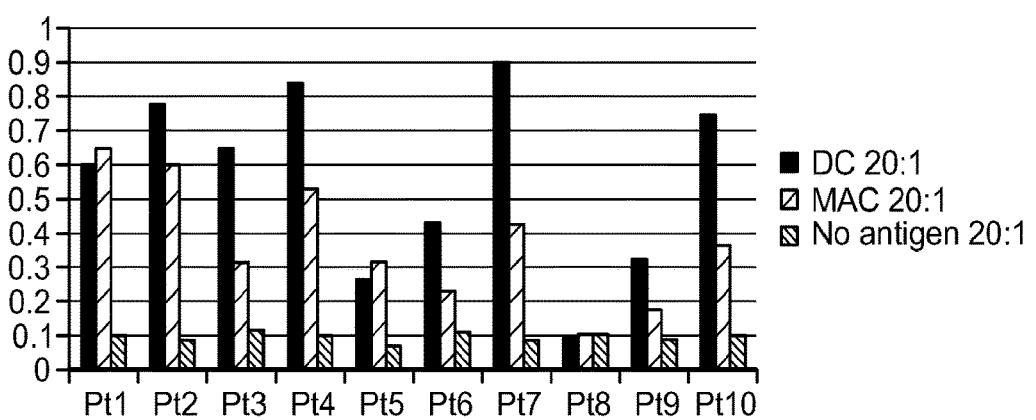

Monocyte-derived dendritic cells are generated in vitro from peripheral blood mononuclear cells (PBMCs) from a patient. In a preferred embodiment, plating of PBMCs for 2 hours in a tissue culture flask permits adherence of monocytes. In an alternative embodiment, $CD14^+$ magnetic beads can be used to isolate dendritic cells from PBMC's (Miltenyi Biotec, Auburn, Calif.). At this point the nonadherent cells are removed and frozen at −80 to later serve as a source of T cells. Treatment of the adherent monocytes with interleukin 4 (IL-4) and granulocyte-macrophage colony stimulating factor (GM-CSF) leads to differentiation to immature dendritic cells (iDCs) in about a week. Subsequent treatment with tumor necrosis factor (TNF) or macrophage conditioned media for 2 days further differentiates the iDCs into mature dendritic cells. These cells are then pulsed with a peptide or a plasmid containing a subdominant antigen for 2 hours and then the PBMC's are thawed and added to the pulsed dendritic cells. After a few hours, the cells are pooled and resuspended in media containing IL-2 or IL-15 (with IL-15 being preferred) to generate in vitro expansion of the T cells which have recognized the antigen. For certain protocols, IL-7 and IL-15 are added to increase T cell survival. For other protocols, culture conditions are adjusted to optimize growth of certain subsets of T cells. For example, IL-12 can be added to polarize to TH1 cells. Alternatively, IL-4 can be added to polarize to TH2. In certain protocols, IL-6 can be added to prevent the growth of Treg. In still another variation which is useful in autoimmune or organ transplantation applications, low level $IL-2^+$ rapamycin can be added to accentuate the growth of Treg. More detailed protocols are outlined in the various examples and in vivo comparison of the cells produced with protocols to polarize the cells to certain T cell subsets is described in Example 3, FIG. 3. If the T cells are grown in a tissue culture flask, media must be replaced at day 14 and day 21. However, in a preferred embodiment, a bioreactor can be used to mitigate this need, e.g., a gas permeable bioreactor such as Grex (Wilson Wolf) or Hyperstack (Corning). Generally, enough cells to be administered to a patient can be generated within 2 to 6 weeks as opposed to 12-24 weeks with traditional methods.

In another embodiment of the invention, the inventors have developed T cells for adoptive transfer against antigens which have been deleted for their dominant epitopes and demonstrate that more T cells are generated to subdominant epitopes. Such proteins or corresponding DNA vaccines can be used to generate T cells with a broad immune response against subdominant epitopes. This approach should be broadly applicable across a wide range of diseases to achieve a balance of the immune response towards subdominant epitopes including but not limited to EBV, cancer, HIV or hepatitis. In another embodiment, the antigen, or a plasmid/recombinant vaccine encoding it, is used to vaccinate the patient to induce a de novo broad immune response to the subdominant antigen. In another embodiment, the subdominant reactive T cells can be administered followed by a vaccination with the subdominant antigen to boost the response. In still another embodiment, the approach could be used therapeutically or prophylactically wherein a patient's immune profile can be determined to measure risk of coming down with diseases and the patient can then be primed to appropriate subdominant antigens using any of the approaches disclosed herein.

In an alternative embodiment, the grown T cells induce tolerance to prevent or treat an autoimmune disease, allergy, inflammation, organ transplantation rejection, or graft versus host disease. Depending upon the type of T cells desired, culture conditions can be modified to preferentially grow, or enrich for, the relevant subset including but not limited to CD8, CD4, TH1, TH2, or Treg. For example, T cells can be grown in presence or absence of certain growth factors, cytokines, drugs, small molecules, or other immune cells. In a preferred embodiment, subdominant antigen reactive T cells are generated from Peripheral Blood Mononuclear Cells (PBMC's) in tissue culture in the presence of a stimulated professional Antigen Presenting Cell (e.g., monocyte derived dendritic cell, macrophage or EBV immortalized B cell).

In another embodiment, various techniques are used to modify antigen processing to favor subdominant epitopes. In one embodiment of the invention, this is accomplished by modification of the antigens to eliminate dominant epitopes, regions which inhibit antigen processing, or to limit the number of dominant or subdominant epitopes presented at one time to an antigen presenting cell. These modifications increase the response and diversity of subdominant epitopes recognized (Example 1, FIG. 5). In an alternative embodiment, the modified LMP1, LMP 2 and EBNA-1 sequences can be delivered to the APC using a viral vector such as adenovirus or vaccinia virus. In the case of other antigens (LMP1 and EBNA-1), eliminating regions of the protein which lead to poor antigen processing greatly enhances the immune response to subdominant epitopes on those antigens (Example 1, FIG. 6). The modified LMP1, LMP2 and EBNA-1 sequences can be delivered to the APC using peptides, proteins, plasmids or viral vectors such as adenovirus or vaccinia.

Figure 7:
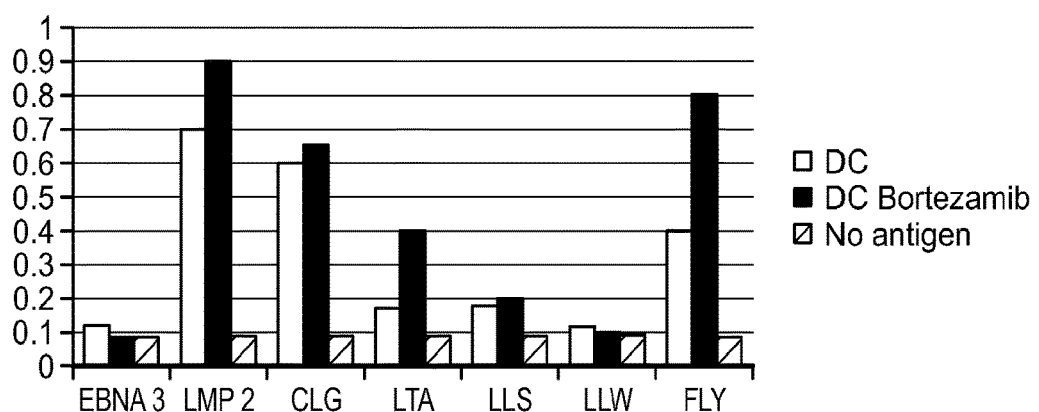

In an alternative embodiment, a proteosome antagonist may be added to the APC's and antigen during CTL production to increase the number of subdominant epitopes recognized and enhance the response to the subdominant antigen (Example 2, FIG. 7). There are many available proteosome antagonists having different mechanisms (e.g., bortezomib, clioquinol, lactacystin, epoxomycin, MG-132, MLN9708, carfilzomib (PR-171)).

Figure 13:
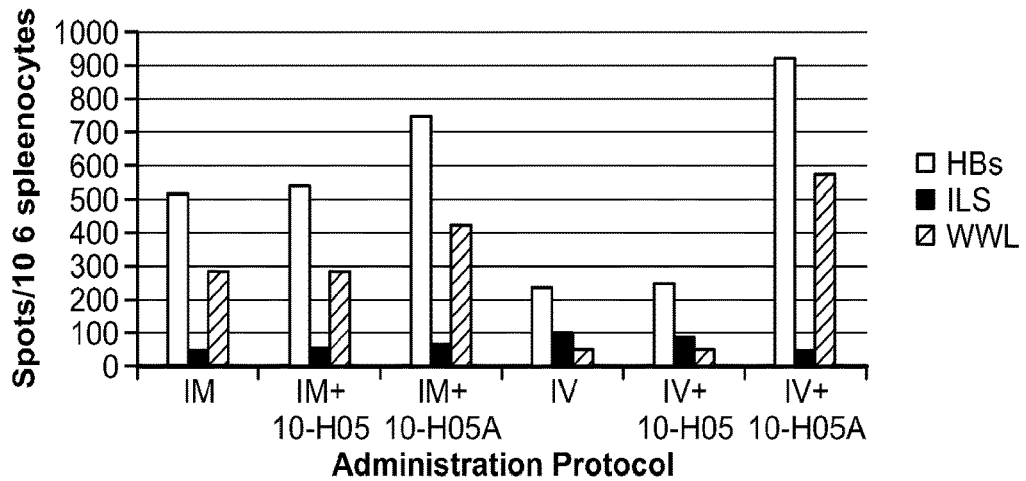

In an alternative embodiment, an antigen may be administered in complexes with antibodies having various isotypes regarding responses to subdominant determinants (Example 3, FIG. 13). The antigen is injected with an antibody binding a determinant flanking the intended T cell epitope to target professional antigen presenting cells and direct antigen processing to the flanking epitopes.

In another embodiment of the present invention, plasmids containing subdominant epitopes or antigens re used to generate T cells which are administered or are directly administered into the patient either directly by various routes of administration, in combination with IFNγ, IL-21 or other cytokines or on pulsed dendritic cells to induce a response to subdominant antigens. IFN-gamma or other cytokines may be induced before T cell stimulation to increase T cell responsiveness to subdominant epitopes and modify the immunodominance hierarchy.

In another embodiment, the route of administration is modified to alter the immunodominance hierarchy. The route of administration of a vaccinia response determines the degree of dominance of the dominant determinant. It has been found that when administered intraperitoneally, the dominant determinant accounted for only a quarter of the response as opposed to half, as was the case with intradermal administration (Tscharke D C et al. 2006, Tscharke D C et al 2005). As shown in Example 3, FIG. 11, administration of antigen by the IM route develops a stronger response and broader response to the subdominant epitope than does IP or IV routes. Thus, modifying the route of administration is another in vivo mechanism which the inventors claim to modify the immunodominance hierarchy. In a preferred embodiment, the T cells cultivated are delivered by intradermal administration. By targeting different APCs (e.g., macrophages, dendritic cells), the route of administration changes the dominance hierarchy (Example 3, FIG. 12).

In a preferred embodiment, the antigens are viral antigens particularly latent viral antigens or chronic viral antigens with subdominant epitopes on them. For example, the viral antigens are from a virus selected from the group comprising: EBV, HSV, VZV, Hepatitis B and C, HIV, and HTLV. The viral antigens are, for example, EBV LMP1, LMP2, EBNA-1, HPV E6, or HPV E7. For example, the viral antigens are associated with EBV, HSV, VZV, Hepatitis B and C, HIV, and HTLV, CMV, RSV, or influenza. In another embodiment, the antigens are antigens on other chronic and latent infectious agents, for example, agents associated with, bacteria, fungi, parasites, or prions. In still another embodiment, the antigens are tumor antigens including but not limited to: tumor associated antigens, tumor specific antigens, antigens associated with cancer stem cells or metastasis. In other embodiments, the antigens are associated with autoimmunity, allergy, inflammation or organ transplantation rejection or graft vs. host disease.

In one embodiment, the immunodominance hierarchy of a patient is altered by identifying a dominant antigen or epitope and a subdominant antigen or epitope in a patient sample, cultivating a T cell capable of recognizing the subdominant antigen or epitope, and treating a patient with an effective number of the T cells.

In one embodiment, the immunodominance hierarchy of a patient is altered by identifying at least one subdominant antigen or epitope in a patient sample, cultivating a T cell capable of recognizing the subdominant antigen or epitope, and treating the patient with an effective number of those T cells to provide therapeutic benefit.

In another embodiment, the T cell is a responsive T cell, and treating a patient with an effective number of said T cell to alter the immunodominance hierarchy of the patient, thereby inducing a cytotoxic immune response in the patient for treatment or prevention of an infection or cancer. The infection is, for example, a bacterial, viral, parasitic, or prion infection.

In any of the methods of the present invention, treatment or prevention of a disease, infection, cancer, or medical condition includes alleviating or ameliorating at least one symptom of the disease, infection, cancer, or medical condition.

D. Therapeutic Methods

1. Cancer

Work Flow of Clinical Use of Immune Profiling of Dominant and Subdominant Antigens
Step 1: Tumor Biopsy (Immunohistochemistry) or Blood (IHC, FACS or Elisa) Antigen 1, 2, 3, 4, 5, 6, 7, 8, 9, 10
  Result: Antigens 1, 2 &6 on tumor, others in panel not
Step 2: Immune Response Profiling

| Humoral Profile | Cellular Profile |
|---|---|
| ELISA on Serum | Elispot or ICS (for IFNg at least, also IL-10, IL-4 and IL-12, IL-21 to assay T cell subsets) on PBMCs stimulated with each antigen |

Result: Antigen 1 strong response (dominant); Antigen 2&6 No/Modest Response (subdominant)
Step 3: Grow T cells (CD8 and CD4) to Subdominant antigens in vitro
  Result: T cells responsive to antigens 2&6
Step 4 (optional once therapy is well established): Confirm >5% T cells grown respond to subdominant antigens using Cellular Immune Profiling (Elispot or ICS)
  Result: 25% of the T cells respond to Antigens 2 & 6
  Providing at least 5% of T cells respond to subdominant antigens, proceed to step 5
Step 5: IV Infuse cells into patient with or without prior conditioning (e.g., cyclophosphamide)
Step 6 (may become optional once therapy is well established): Isolate PBMC's from Blood 2-3 weeks post infusion and Profile Immune Response
  Result: Cellular Profile Antigen 1 No/Moderate response; Antigens 2 & Strong response (dominant) to at least 1 of the antigens
Step 7: Assess Clinical responses
  RECIST (CR, PR); Survival or Progression Free Survival
  Result: Improved response rate and survival In Example 4, this systematic method is used to treat melanoma. In Example 5, the method is applied to treat lymphoma with the multiplasmid LMP2. In fact the T cell therapy changes the natural course of lymphoma from one that is relapsing remitting to one that is a durable remission. This antigen as well as deleted LMP1 and EBNA-1 can also be used to treat other tumors that include EBV antigens including Nasopharyngeal carcinoma, Burkitts Lymphoma, CLL, Hodgkins, and some gastric cancer among others. In Example 3, a similar method is used to treat Hepatocellular carcinoma. These examples are incorporated into the invention by reference and demonstrate that rebalancing of the immune response towards subdominant antigens is broadly applicable to all forms of cancer.

2. General Use of a Large Number of Subdominant Antigens on a Tumor to Produce a Pan Tumor Type Therapy In another embodiment, the inventors propose that if enough subdominant antigens can be identified for a particular type of tumor, that that type of tumor could be treated with T cells to multiple subdominant antigens without the need to test the patient. Similarly, targeting multiple antigens on the same tumor would decrease resistance, e.g., combination chemotherapy. For example, the ability to develop a single T cell line targeting the subdominant antigens EBV LMP2 which is on 40% of lymphomas and surviving (which is on 50% of lymphomas) would allow one to target approximately 80% of lymphomas with a T cell line specific to these 2 antigens. Clinical testing of the Pan-lymphoma product is demonstrated in Example 5. By year 3, progression free survival of patients treated with the Pan lymphoma product is comparable to the product where antigens were tested before therapy. This could be because, like combination chemotherapy, the response of CTL's to multiple antigens on the same tumor could decrease the likelihood of escape. The ability to treat all lymphoma (not having to only treat that subset which is positive for a single antigen) with a single T cell product is a novel product concept. In other embodiments of the invention, the inventors also claim similar Pan-cancer products for virtually any cancer.

3. Chronic Infections

Hepatitis and Hepatocellular Carcinoma

In patients with chronic Hepatitis, HBs antibodies are not generated but HBc antibodies are (Ganem D et al 2004). In patients with acute hepatitis, antibodies to both antigens are generated. >90% of neonates and 30% of children ages 1-5 develop the chronic form while adults acutely clear the virus >90% of the time. 95% of Hepatocellular carcinoma is associated with chronic infection with Hepatitis B virus and. HBsAg often is on the cell surface of HCC. Given these observations, the inventors chose to study whether HBs was subdominant in hepatitis and hepatocellular carcinoma patients and if the growth of T cells could generate CTLs to HBs antigen which could rebalance the immune response to subdominant antigens and be therapeutic.

Based upon this finding, we administered the CTL's grown to HBs Ag to treat chronic hepatitis in an animal model of hepatitis and ultimately in HBV associated HCC patients. In the animal model, HBVtgRAG cells were administered and the tested. In the animal which received control cells, chronic Hepatitis developed. Furthermore, when the animal developed hepatitis and received CTL's to subdominant antigens, the animal developed acute hepatitis but cleared the hepatitis virus (Example 3, FIGS. 9-11).

Given the encouraging animal data, patients with hepatitis were treated with the T cell rebalancing therapy.

Work Flow of Clinical Use of Immune Profiling of Dominant and Subdominant antigens
Step 1: Immune Response Profiling Hepatitis Surface Antigen and Hepatitis Core Antigen

| Humoral Profile | Cellular Profile |
|---|---|
| ELISA on Serum | Elispot or ICS (for IFNγ at least, also IL-10, IL-4 and IL-12, IL-21 to assay T cell subsets) on PBMCs stimulated with antigen |

Result: Hbc strong response (dominant); Hbs No/Modest Response (subdominant)
Step 2: Grow T cells (CD8 and CD4) to Subdominant antigen in vitro
  Result: T cells responsive to HBs antigen
Step 3 (optional once therapy is well established): Confirm >5% T cells grown respond to subdominant antigen using Cellular Immune Profiling (Elispot or ICS)
  Result: 25% of the T cells respond to HBs Antigen
  Providing at least 5% of T cells respond to subdominant antigens, proceed to step 4
Step 4: IV Infuse cells into patient with or without prior conditioning (e.g., cyclophosphamide)

Step 5 (may become optional once therapy is well established): Isolate PBMC's from Blood 2-3 weeks post infusion and Profile Immune Response Result: Cellular Profile HBc No/Moderate response; HBs Strong response (dominant)

Step 6: Assess Clinical responses

Result: Clearance of Infection

Immune profiling was conducted on 5 patients with HBV and HCC. As expected, ELISA demonstrated high titers of antibody to hepatitis B core antigen (HBc Ag) but not to hepatitis B surface antigen (HBs Ag) (Example 3, FIG. 17). However, when PBMC's were induced into dendritic cells, pulsed with hepatitis B core antigen (HBc Ag) and hepatitis B surface antigen (HBs Ag) and used to grow CTL's from PBMC's from the same patient, a surprising result was observed. By frequency of IFN producing T cells on Elispot a hierarchy was observed: no-antigen (10 sfc)<HBsAg (15 sfc)<HBcAg (45 sfc) (Example 3, FIG. 14). This indicates that Hepatitis B surface antigen was indeed subdominant relative to Hepatitis core. Furthermore, it appeared that one epitope (FLL) of HBs was dominant by Elispot (Example 3, FIG. 14) and by ICS (Example 3, FIG. 15). The peptide containing this epitope was excluded from the pepmix that was used to grow cells from that patient.

Figure 16:
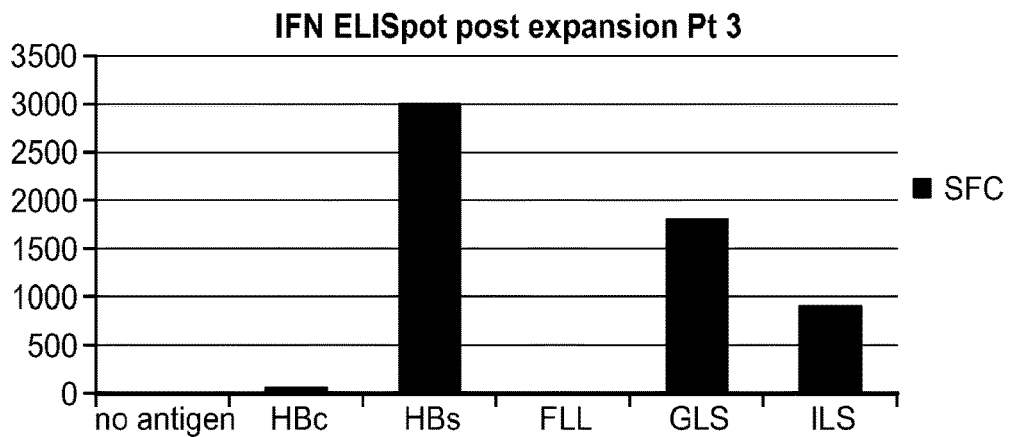
FIG. 16 shows a hierarchy of antigens.
Figure 17:
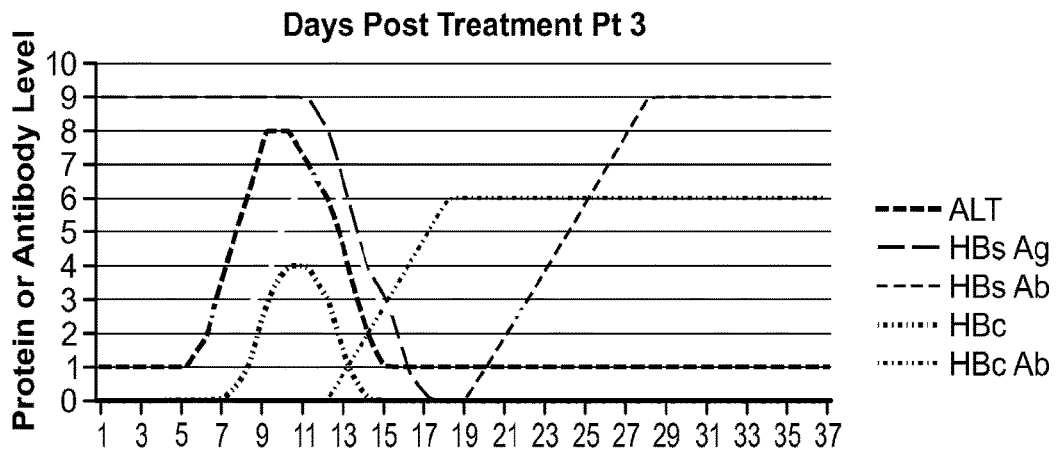
FIG. 17 shows immune response following an acute flair, then clearance of hepatitis.
Figure 18:
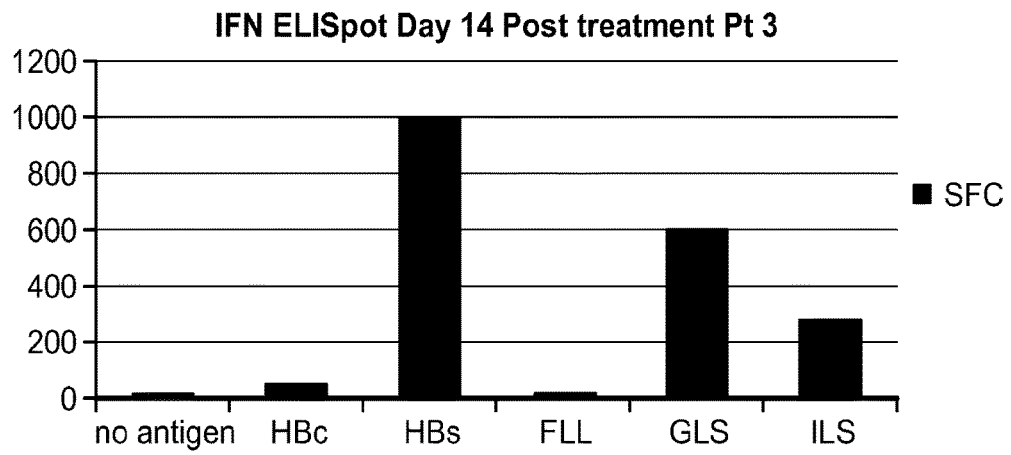
FIG. 18 shows a hierarchy of antigens following the clearance.
Figure 19:
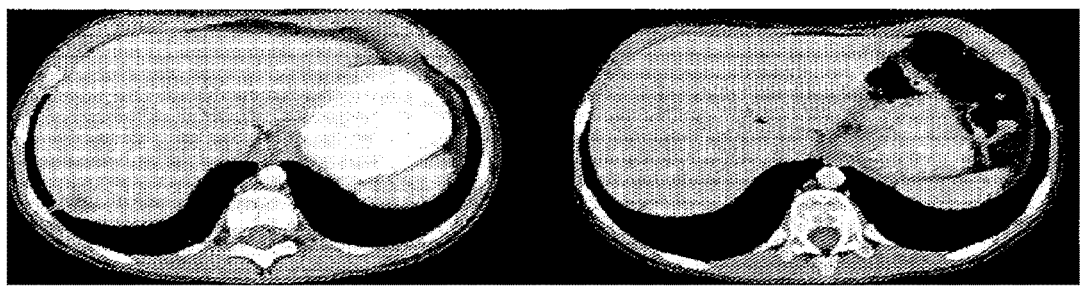
FIG. 19 shows that the T cells completely resolved the patient's Hepatocellular carcinoma (before treatment—left; 8 weeks post-therapy—right).

In patients with HCC, 3/5 patients who received the T cells to subdominant HBs (Example 3, FIG. 16) cleared the HBs antigen and demonstrated CR's to the HCC following a transient elevation of Alanine transaminase (ALT) in Liver Function Tests (Example 3, FIGS. 17 & 19). When PBMC's from those patients were tested 2 weeks post administration, the dominant response was to HBs rather than to HBc and to the previously subdominant epitopes of HBs (Example 3, FIG. 18) indicating that the patients had rebalanced their immunodominance hierarchy. As a result of the therapy and the switch in immunodominance hierarchy was providing the therapeutic benefit (Example 3, FIGS. 17 & 19).

Thus, T cell adoptive immunotherapy to subdominant antigens can be used to eradicate chronic viruses and to treat cancers on which they are present. Further, immune profiling to direct the production of T cells to subdominant antigens and epitope opens a novel therapeutic avenue in multiple diseases.

Virtually any viral, bacterial, fungal, prion, parasitic or other infectious disease can be treated including but are not limited to Hepatitis C virus and HIV virus. Other chronic infectious disease can also be treated using rebalancing. For example, Mycobacterial tuberculosis is a chronic infection in many patients but only reactivates when the immune system is repressed. In its dormant state, it is contained by a granuloma usually in the lung. Recent studies of the proteome of the mycobacterial phagosome indicate that MTB represses antigen presentation in dendritic cells to a greater degree than macrophages (Li et al. 2011). To this end the inventors proposed that rebalancing the immune system to respond to subdominant epitopes is a broad therapeutic approach for virtually any cancer or infectious disease.

4. Autoimmunity

Epidemiological studies demonstrate that the risk of patients developing multiple sclerosis correlates with EBV antibody titers. By following hundreds of thousands of individuals before they were infected with EBV and following up with them for several years post initial infection, Ascherio et al. were able to study the 305 patients who developed MS. Their risk increased sharply following EBV infection (Ascherio A et al. 2010). Memory CTL's responsive to EBNA-1 400-641 were elevated in MS patients relative to other EBV antigens when compared to healthy individuals who were also EBV carriers (Lunemann J D et al. 2006). EBNA-1 specific Th1 cells appear capable of sustaining autoimmunity by cross recognition of auto-antigens or bystander mechanisms. Further, transgenic mouse studies suggest that B cells expressing LMP2a bypass normal tolerance checkpoints and enhances development of autoimmune disease (Swanson-Mungerson M 2007). As such, while we have studied T cells reactive to EBV subdominant epitopes as a treatment for EBV and EBV related cancers, T cells reactive to EBV subdominant epitopes may also be useful in reinstating balance in autoimmunity. By growing and introducing the T cells responsive to EBV latent antigens (EBNA-1, LMP1 and LMP2), the inventors propose that the immune response can be rebalanced, reinducing tolerance in the autoimmune diseases with an EBV association. The same would hold true for other viruses associated with other autoimmune disease. For example, Picornaviruses such as Coxsackievirus B3 cause myocarditis/dilated cardiomyopathy, type 1 diabetes, encephalitis, myositis, orchitis, hepatitis.

In still other embodiments, T cells can be generated against antigens associated with organs in which organ specific autoimmunity is developed. Because the phenomenon of immunodominance involves epitopes from all of the antigens which are being processed at any one time, there is not a completely required need to know the exact autoantigen which is driving the autoimmune response at that time. For example, generating and introducing T cells to reactive subdominant epitopes of collagen into the inflamed joint of rheumatoid arthritis patients, the ongoing immune response will be rebalanced and tolerance will be reinstated. It is contrarian and unexpected to think that introducing active T cells into an inflammatory site would be beneficial, but according to our operative model, the rebalancing of the immune response in that site will reinstate appropriate control over the aberrant immune response. The treatment of autoimmune diseases is another embodiment of the invention.

5. Treg In Vitro Expansion

One of the principles of immune regulation is the balance of Tregs to other subsets of T cells. Another embodiment of the invention is polarizing the ex vivo T cell growth towards Treg cells. In this case, instead of targeting subdominant epitopes, Treg to dominant epitopes are generated as another way to rebalance the immune response. In one embodiment, the Treg T cells so generated are used as the therapeutic product alone. In another embodiment, the Treg subset is used in combination with T cells from other subsets grown to subdominant epitopes or subdominant antigens While Tregs have been expanded in a non antigen specific way using FACS sorting followed by expansion with anti-CD23 and anti-CD28 coated beads (Putnam et al. 2009), to date no one has expanded Tregs in an antigen specific way for adoptive immunotherapy. Described herein are methods which are useful in the establishment of Tregs specific for different antigens especially those which are dominant in the immune response observed in autoimmune disease, graft vs. host disease or transplant rejection.

Tregs were isolated from PBMC's of autoimmune or Transplant patients by FACS sorting (BD FACS Aria II high speed cell sorter) using an aseptic technique in a GMP clean room using CD4-PerCP(SK3), CD127-PE (hIL-7R-M21), CD25 APC (2A3), CD45RA-PE.Cy7 (L48) and CD45RO-PE.Cy5 (UCHLI). $CD4^+$ $CD127^{lo/-}CD25^+$ and $CD4^+$ $CD127^{lo/-}$ T cells were sorted and collected in 3 ml X-Vivo 15 media (Lonza, Walkersville, Md.) containing 10% human heat-inactivated pooled AB serum (Valley Biomedical, Winchester, Va.). (Alternatively, Tregs can be separated using magnetic beads coated with the same antibodies (Miltenyi Biotec, Auburn, Calif.). These cell were plated at $2.5 \times 10^5$ Tregs per well in a 24 well plate (Costar, Cambridge, Mass.), each well containing dendritic cells prepared from the PBMC's (as described for T cell stimulation above) which had been pre-pulsed with dominant antigen at a Treg:APC ratio of 1:5. Following 18 hours incubation, cells received rapamycin (100 ng/ml; Wyeth, Madison, N.J.), from day 1 to 7 in culture. At day 2, culture volume was doubled and 300 units/ml IL-2 was added (Chiron, Emeryville, Calif.). Cells were resuspended and fresh media and IL-2 were added days 2, 5, 7, 9 and 12. On day 9 cells were restimulated with peptide pulsed dendritic cells. Alternatively, anti-CD23/anti-CD28 coated microbeads (Invitrogen, Carlsbad, Calif.) can be used for this second stimulation. Further, the gas permeable bioreactor (such as Grex) can be used to perform this cell growth with fewer manipulations in a closed system and improve the kinetics of growth. In another variation IL-10 is added at the time of stimulation with the coated beads to drive further differentiation of the Treg to Treg 1 which secrete high levels of IL-10 and regulate TH1 and Th2 responses.

Work Flow of Clinical Use of Immune Profiling of Dominant and Subdominant Antigens in Autoimmunity
Step 1: Immune Response Profiling

| Humoral Profile | Cellular Profile |
|---|---|
| ELISA on Serum | Elispot or ICS (for IFNγ at least, also IL-10, IL-4 and IL-12, IL-21 to assay T cell subsets) on PBMCs stimulated with each antigen |

Result: Antigen 1 strong response (dominant); Antigen 2 No/Modest Response (subdominant)
Step 2: Grow T cells (CD8 and CD4) to Subdominant antigens in vitro; Grow Treg to dominant antigens in vitro
Result: T cells responsive to subdominant antigens; Treg responsive to dominant antigens
Step 3 (optional once therapy is well established): Confirm >5% T cells grown respond to subdominant antigens and Treg grow to dominant antigens using Cellular Immune Profiling (Elispot or ICS)
Result: 25% of the T cells respond to Antigens
Providing at least 5% of T cells respond to subdominant antigens and/or at least 5% of Treg cells respond to dominant antigen, proceed to step 4
Step 4: IV Infuse cells into patient with or without prior conditioning (e.g., cyclophosphamide)
Step 5 (may become optional once therapy is well established): Isolate PBMC's from Blood 2-3 weeks post infusion and Profile Immune Response
Result: Cellular Profile Antigen 1 No/Moderate effector response; Antigens 2 & Strong Treg response (dominant)
Step 6: Assess Clinical responses
In autoimmunity (MS—flare ups decrease, Rheumatoid Arthritis—joint swelling reduced, Asthma—number of attacks decreases, Early Type I diabetes, pancreas is maintained), In transplant-organ rejection rate and Graft vs. host disease decrease
Result: Improved clinical outcome
6. Administration of Tregs to Dominant Antigens in Autoimmunity or Transplant
In still another embodiment, Treg against dominant antigens could be combined with T cell of the TH1, TH2 or CTL subsets which are themselves responsive to subdominant antigens. Such a combination would more fully switch the balance of the response towards subdominant epitopes. The inventors have demonstrated synergy between the two types of T cells in arthritis (Example 6).

7. Transplant
In an alternative embodiment, Treg are grown using the above Treg culture conditions from PBMC's of healthy donors using dendritic cells (or irradiated PBMC's) from other healthy donors. In this way alloreactive Treg lines to each of the MHC are established and banked. As we discussed above, 80% of the MHC could be covered with Treg lines generated against 20 to 50 MHC haplotypes. Each of these lines could be frozen in single dose aliquots at −80 degrees C. When an organ or BMT is performed, $5 \times 10^7$ cells/m$^2$ Treg reactive to the mismatched MHC are also transplanted into the patient. In this way, the allogeneic rejection or graft vs. host disease is mitigated.

8. Automated Immune Profiling Assays and Closed System Cell Culture Device
Gas permeable membrane devices are a preferred embodiment of the culture techniques. Because the membrane is gas permeable, the scale of the culture is determined by the surface area of the membrane and the volume of media required to grow the cells. Examples of these gas permeable devices include Hyperstack (Corning) or Grex (Wilson Wolf). One of the useful features of this type of bioreactor is that the cell culture process is linearly scaleable. As part of the standardization of our approach, we have designed versions of bioreactors which slide into standard $CO_2$ incubators for use in production suites. In a separate embodiment, we have designed bioreactors which fit into standard stacks for warm rooms in an automated production facility The bioreactors intended for automation are made in two sizes: one for growth of autologous cells for an individual patient and a second larger version for the commercial production of allogeneic T cell lines. In an improved method, the cell culture devices are modified for automation into a rectangular shape so as to slide into the slots on a standard $CO_2$ incubator. This is a significant advantage as the gas permeable membrane is on the bottom of the flask and hence is blocked if it is sitting on the shelf. By having the flask be the shelf, there is better airflow to the membrane. A key attribute is the flanges on the side of the flask which allow them to hold the weight of the bioreactor. In one embodiment, the bioreactor sets into a stainless steel frame which forms slides into the shelf supports. In another embodiment, they are molded as part of the plastic. In one of the embodiments, they have the footprint of an entire shelf. In another embodiment, they comprise ½, ¼ or ⅓ Or ⅕ of a shelf. In a preferred embodiment, the incubator is made by New Brunswick, Forma, ThermoElectron, Nuaire, ESCO. In a preferred embodiment, the incubator can be air or water jacketed or other design. In still another embodiment, they fit within a shelf which is a metal frame or on a flat in a warm room. In another preferred embodiment, the flat is moved and processed robotically. In still another embodiment, the bioreactor fits various commercial processing equipment including but not limited to a rocker which brings the cells back into suspension prior to harvesting.

Figure 31:
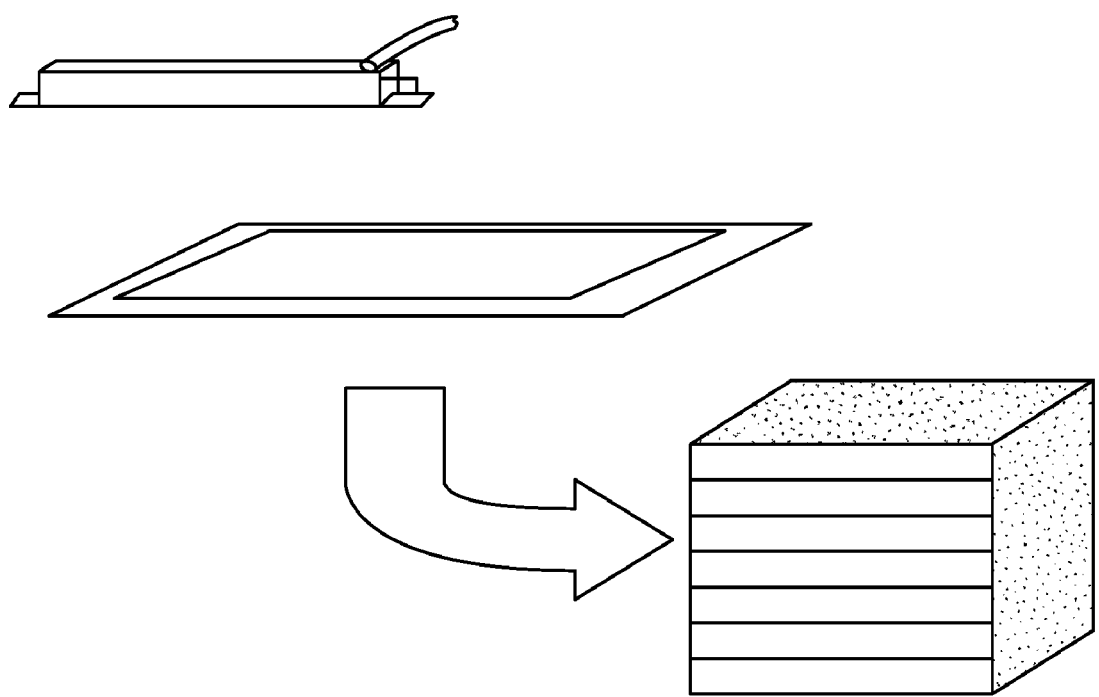
FIG. 31 is a schematic of a bioreactor for use with the therapy of the present invention.

Each bioreactor is a closed system with access ports to introduce media, components and cells and from which to harvest the cells for freezing and quality control. In a preferred embodiment, these access ports are tubing which ports fluids and cells in and out of the bioreactor the cap for which has integrated solid tubes which reach the bottom of the bioreactor. In an alternative embodiment, the access port is a sterile sheet of rubber through which a needle or other probe can be inserted into the bioreactor to inject or remove fluid cells or other reagents either manually or using an automated robot. The devices are bar coded in order to track them so that each patient and each cell line will have its own dedicated bioreactor. The bioreactor is disposable after it has been used. The bioreactors are also sized to fit standard robotic automation equipment in automated cell culture including but not limited to stacks, transporters and rocking agitators. FIG. 31 is an example of such a bioreactor.

Like the bioreactors, commercial multiplexed immune profiling assays are also designed to enable processing of measuring titers of antibodies and T cell responses to panels of antigens. In order to do this, the ELISPOT assay is used as standard 96 well plate format can be applied. In a preferred embodiment, the AIDELISPOT reader (Autoimmun Diagnostika, Strassberg, Germany) is used to count the spots. Alternatively, the 96 well plate is used to input cells into the FACS for the ICS assay. In any event, each patient has their own dedicated 96 well plate which is bar coded and all plates are disposable. These commercial assays and manufacturing processes are embodiments of the invention.

E. EXAMPLES

1. Example 1: EBV Latent Infection, Lymphomas and Nasopharyngial Carcinoma

90% of the world's population has been exposed to EBV (the causative virus in mononucleosis) as measured by antibodies in the blood. EBV becomes latent in B cells and shuts off the majority of its proteins but express very low levels of latent antigens LMP1, LMP2 and sometimes EBNA-1. These proteins are weakly immunogenic but are required to maintain the virus even in its latent state. Because they derive predominantly from B cells, 40% of lymphomas test positive for EBV latent antigens. Thus, these antigens can serve as targets for the generation of CTL responses in adoptive cell therapy. In addition, Nasopharyngial carcinoma also expresses EBV latent antigens as do other tumors (e.g. ~10% of gastric cancer). While CTL's have been used to treat EBV lymphomas, the current production methods are time consuming (3-6 months) and cumbersome using B cells transformed with EBV as repeat stimulation. Further, CTL's made in this way to LMP2 produced T cell batches only half of which had a detectable response to LMP2 post production. The inventors believed that the reasons for this were due to the presence of dominant epitopes from EBV proteins in the EBV transformed LCL cells which generated CTL's which outgrew the cells against LMP2 50% of the time. In patients with bulky tumors, 52% of the patients treated with CTL's produced by the traditional process had a complete response. While the prior art considered all CTL's equivalent regardless of the presence or lack of response to LMP2, the inventors felt that this may be one reason for the variable clinical response. Furthermore, the operative model of the invention predicted that this was indeed the case. Hence increasing the efficiency of CTL generation to LMP2 may be clinically important.

While other methods of CTL production are also embodied in the invention, the following methods were used to create the following experimental data: 40 ml to 100 ml of peripheral blood was collected from the patients in Vacutainer tubes. Peripheral Blood Mononuclear cells (PBMC's) were isolated by centrifugation on Lymphoprep (Nycomed, Oslo, Norway), resuspended in RPMI 1640 (Gibco, Grand Island, N.Y.) including 2 mM L glutamine, 100 IU/ml penicillin, 100 µg streptomycin/ml, with 10% Fetal calf serum (FCS) ($5\times10^6$ cells/ml) and seeded onto 6 well plates (Costar Corp, Cambridge, Mass.) at $10^7$ cells/well. After 2 hours at 37 degrees C., nonadherent cells were removed and resuspended in FCS with 10% polyethylene glycol (PEG) placed in test tubes, frozen on dry ice and stored in a −80 freezer. The adherent cells still in the 6 well plate was cultured in RPMI+10% FCS supplemented with 50 ng of GM-CSF and 1000 U of IL-4 per ml. Half of the media was replaced with fresh media including the same growth factors described above on day 2 and day 4. On day 6, the media was completely replaced with the media described as well as the addition of 25% volume of macrophage conditioned medium to stimulate maturation. Macrophage conditioned media was produced by PBMCs adherent to immunoglobulin coated plates (prepared by immunoglobulin in PBS, plating and incubating at 4 degrees C. overnight) for 24 hours at 37 degrees C. in RPMI 10% FCS, harvesting the supernatant, filtration through a 0.2 mm pore size membrane (Acrodisc, Gelman Sciences) and storage at −20 degrees C. for up to 8 weeks before use. Nonadherent cells were harvested 2 days later and used as a source of dendritic cells. Immunofluorescence staining with monoclonal antibodies for surface markers including CD54, CD80, CD83 and CD86 was performed to assure dendritic cell quality (>50% of cells+).

DC stimulators were preexposed for 2 hours at 37 degrees C. to proteins at a concentration of µg/ml (50 for peptides) in serum free RPMI 1640 supplemented with human 132 microglobulin at 3 µg/ml. They were then washed and seeded at $10^5$ cells/2 ml well in RPMI 10% FCS supplemented with IL-7 5 ng/ml. $2\times10^6$ PBMC's were added to each well for a responder to stimulator ratio of 20:1. The cultures were restimulated (and split into additional wells, if necessary) on days 14 and 21 with autologous peptide loaded dendritic cells in RPMI 10% FCS supplemented with IL-2 at 20 U/ml.

Release testing of CTL's to be used for treating patients included viability of >70%, negative culture for bacteria and fungi after 7 days, endotoxin testing less than 5 EU/ml, negative results for *Mycoplasma*, less than 20% killing of recipient lymphoblasts at a 20:1 ratio in $^{51}Cr$ release assays, less than 2% $CD19^+$ B cells, less than 2% $CD14^+$ monocytes and HLA identity.

Polyclonal T cell populations were harvested and used as effectors in a 5 hr chromium release assay. For the chromium release assays, monolayer cultures of fibroblasts established from skin biopsies of CTL donors and exposed to recombinant vaccinia virus ($2\times10^6$ cells per 9 cm petri dish) Cells harvested 18 hours post transfection and labeled for 1 hour with $^{51}CrO_4$, washed three times, and used as targets in a 5 hour chromium release assay. Supernatants from the assay were harvested into 1% formaldehyde before counting on a 7 counter.

a. Experiment 1: The Relative Frequency of T Cells Responding to Subdominant Epitopes is Enhanced when Dendritic Cells or Activated Macrophages are Used as Antigen Presenting Cells Instead of LCL T cell lines were prepared from 10 patients using 3 different antigen presenting cells as stimulators: EBV transformed lymphoblastoid cell lines (LCL) presentation and expansion; Dendritic cell (DC) presentation with cytokine expansion; IFNγ Macrophage (MAC) presentation with cytokine expansion. Each of the 3 were stimulated during antigen presentation with a mixture of 3 plasmids expressing subdominant epitopes of EBNA-1 (EBNA-1 with deletion of aa 90 to 325), LMP1 (LMP1 with deletion of aa 1-43 and aa 260-315) and LMP2 (LMP2A in 2 plasmids one expressing aa 1-399 and the second plasmid expressing aa 400-497). The T cell lines so generated using the protocol of the invention were then studied in $^{51}$Cr release assay.

Figure 1B:
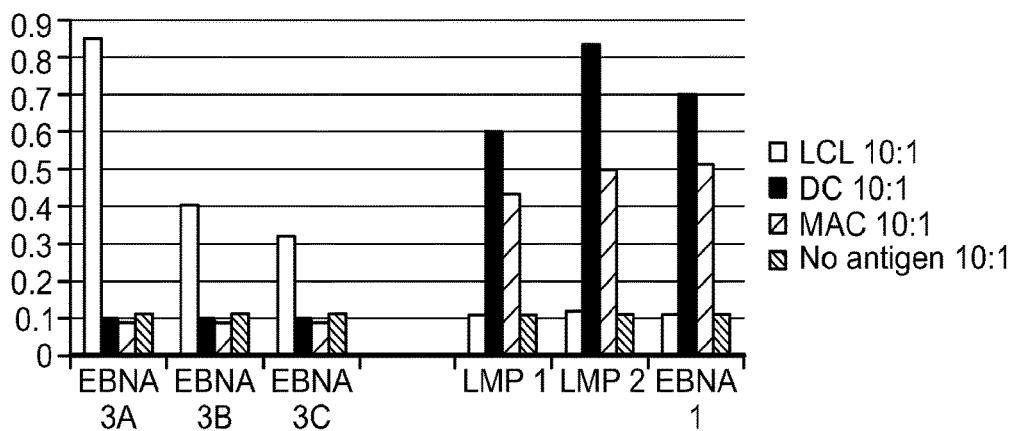

FIGS. 1A and 1B: $^{51}$Cr release at two different effector: target (E/T) ratios, 20:1 and 10:1, respectively, (CTL line: HLA matched fibroblasts) HLA matched fibroblasts pre-pulsed with peptide mixes from the indicated antigens, CTL's expanded from representative patient using different indicated APC's to grow CTL line.

Conclusion: Dendritic cells (DC) and Macrophages (MAC) more selectively stimulate the growth of CTL's to subdominant antigens than EBV transformed B cells (LCL's).

Figure 1C:
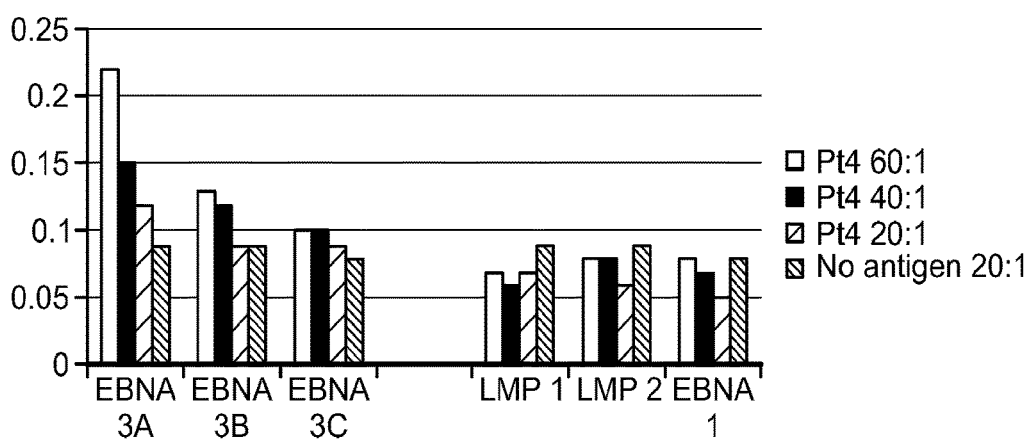

FIG. 1C: $^{51}$Cr release at three different effector:target (E/T) ratios (CTL's: HLA matched fibroblasts) HLA matched fibroblasts pre-pulsed with peptide mixes from the indicated antigens CTL's from PBMC's of the same patient directly after blood harvested (before culture).

Figure 2:
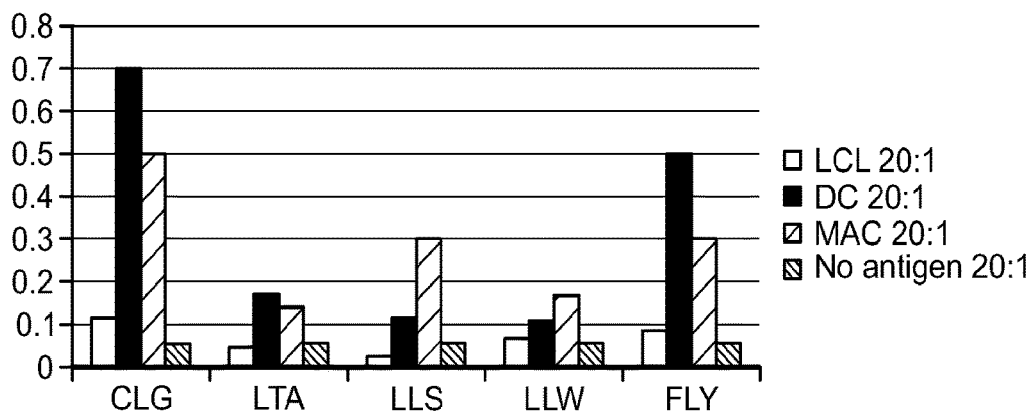
FIG. 2 shows the results of a $^{51}$Cr release assay.

Conclusion: Patients have some response to EBV dominant antigens but at significantly higher E/T ratios than after T cell culture FIG. 2: $^{51}$Cr release at 20:1 effector:target (E/T) ratios (CTL Lines: HLA matched fibroblasts) HLA matched fibroblasts pre-pulsed with peptides representing specific HLA A2 restricted subdominant epitopes from LMP2 with CTLs made from the same patient using three different methods as above:

Conclusion: Dendritic cells and Macrophages both lead to a response to a broader number of subdominant epitopes & higher levels of CTL activity than does LCL and the magnitude of the response to different epitopes is different between the Dendritic cells and Macrophages FIGS. 3A and 3B: $^{51}$Cr release at 20:1 effector:target (E/T) ratios (CTL Lines: HLA matched fibroblasts) HLA matched fibroblasts pre-pulsed with peptides from LMP2: LCL Stimulation in FIG. 3A and DC/MAC stimulation in FIG. 3B.

Conclusion: Dendritic cells and Macrophages lead to CTL Lines in 90% of the patients, in contrast to the LCL which only led to 50% of the CTL lines from the patients having a detectable LMP2 response. Therefore, the DC/MAC process is more robust and reproducible for generating T cells to subdominant antigens and epitopes.

Figure 3C:
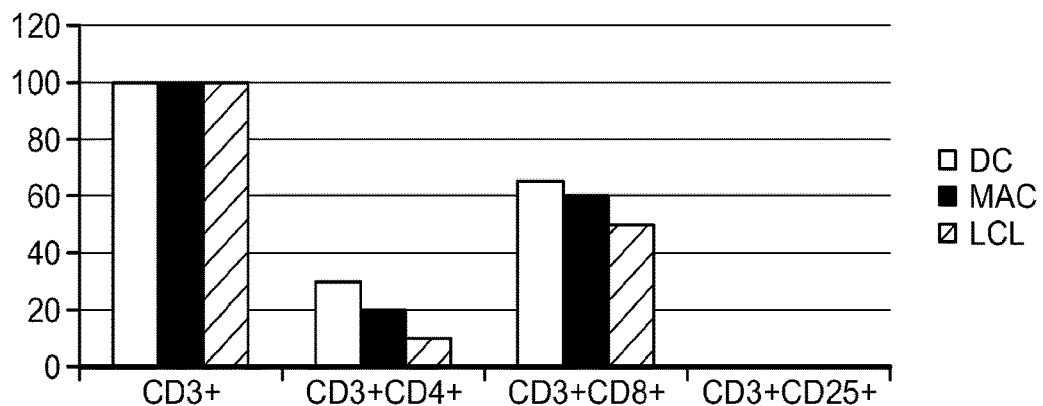
FIG. 3C shows the percentage of viable APCs.

FIG. 3C: % of Viable CD3$^+$ Cells which are CD4$^+$, CD8$^+$ and CD25$^+$ in CTL Lines grown using Macrophage, Dendritic Cells or LCL cells as Antigen Presenting Cells. Lines were stained with antibodies for CD3, CD4, CD8 and CD25 and analyzed by Flow Cytometry.

Conclusion: While all methods establish CD8$^+$ cells and not Tregs, the use of Dendritic cells and macrophages as APC's appears to increase the % of CD4$^+$ cells relative to that produced with LCLs.

ELISpot Assays:

Elispot assays were performed to determine the number of T cells produced to particular antigens. Elispot γ IFN 96 well polyvinylidene diflouride backed plates (Millipore, Bedford, Mass.) were coated with 15 µg/ml of anti-IFNγ monoclonal antibody 1-DIK (MABTECH, Stockholm, Sweden). 5×10$^6$ PBMCs were added per well with peptide mixes 2 µM each from each of the proteins and incubated overnight at 37 degrees C. 5% $CO_2$. Cells were discarded and 1 µg/ml biotinylated anti-IFNγ monoclonal antibody 7-B6-1 (MABTECH) was incubated 2-4 hours at room temperature followed by streptavidin conjugated alkaline phosphatase (MABTECH) for 2 more hours. After a 30 minute reaction with 5-bromo-4-chloro-3-indolyl phosphate and nitro blue tetrazolium from the alk-phos substrate kit (Bio-Rad Richmond, Calif.), depending upon the number of samples, the spots were counted either using a dissection microscope or on an AIDELISPOT reader (Autoimmun Diagnostika, Strassberg, Germany). Each spot was a cell reported as spot forming cells (SFC)/10$^5$ PBMC's. In these assays, the positive control was cells+10 µg/ml PHA and negative control was cells alone without peptide.

Figure 4:
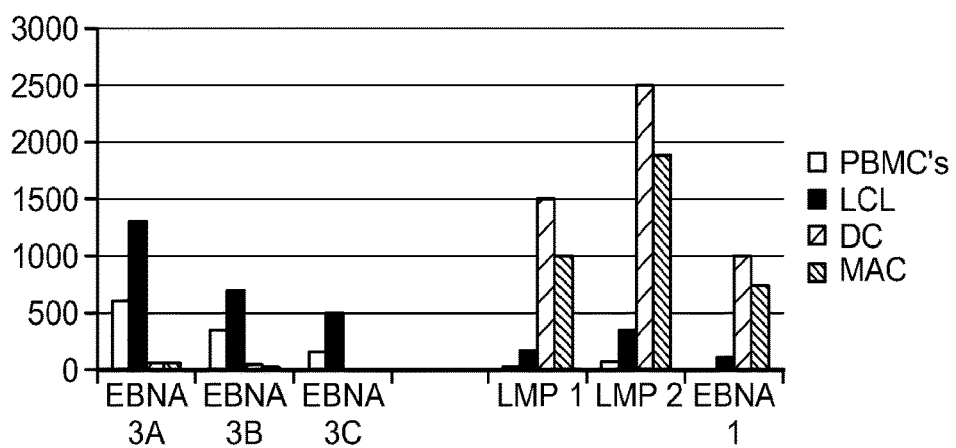
FIG. 4 shows IFNγ producing cells measured by Elispot.

FIG. 4: IFN producing cells (SFC's)/105 T cells grown in vitro as measured by Elispot Conclusion: Dendritic cells and Macrophages more selectively expand T cells to subdominant antigens than LCL Optimizing Antigens to Establish Responses to Subdominant Epitopes LMP2 was chosen for optimization as it is a subdominant antigen relative to EBNA-3 and the majority of EBV subdominant epitopes recognized appeared to be on this protein as identified using consensus software and PBMC testing. In an effort to increase the number of subdominant epitopes recognized, LMP2 was split onto two or more plasmids. The following plasmids were constructed in the p shuttle or pUC19 plasmid under control of the CMV promoter and artificial ATG and poly A:

Plasmid 1 LMP2B (aa 1-497)
Plasmid 2 LMP2A 1$^{st}$ exon (aa 1-119)
Plasmid 3 LMP2A 2$^{nd}$ exon (aa 120-497)
Plasmid 4 LMP2A (aa 120-399)
Plasmid 5 LMP2A (aa 400-497)
Plasmid 6 LMP2A (aa 120-440)
Plasmid 7 LMP2A (aa440-497)
Plasmid 8 LMP2A (aa 1-399)
Plasmid 9 LMP2A (aa400-497)

All plasmids were generated using standard procedures in SCS110 bacteria strains (Stratagene, La Jolla, Calif.) and purified with Endo free Plasmid Maxi kit (Qiagen, Hilden, Germany). Antigen presenting cells were transfected 24 hours after maturation using the Amaxa DC Nucleofection Kit (Amaxa, Koeln, Germany) with 2-20 µg plasmid DNA per 10$^6$ cells.

T cell immunosubdominant epitopes on LMP2 include but are not limited to:
LLW 329-337 LLWTLVVLL HLA A 2.01 (SEQ ID NO:1)
CLG 426-434 CLGGLLTMV HLA A 2.01 (SEQ ID NO:2)
IED 200-208 IEDPPFNSL HLA B 40.01 (SEQ ID NO:3)
SSC 340-350 SSCSSCPLSKI HLA A11.01 (SEQ ID NO:4)
TYG 419-427 TYGPVFMCL HLA A24.02 (SEQ ID NO:5)
LLS 447-455 LLSAWILTA HLA A2 (SEQ ID NO:6)
LTA 453 461 LTAGFLIFL HLA A2 (SEQ ID NO:7)
FLY 356-364 FLYALALL HLA A2 (SEQ ID NO:8)

Peptides for these epitopes were synthesized and used to test CTL responses in $^{51}$Cr release assays on HLA-A2 expressing fibroblasts isolated from skin of PBMC donors.

Figure 5:
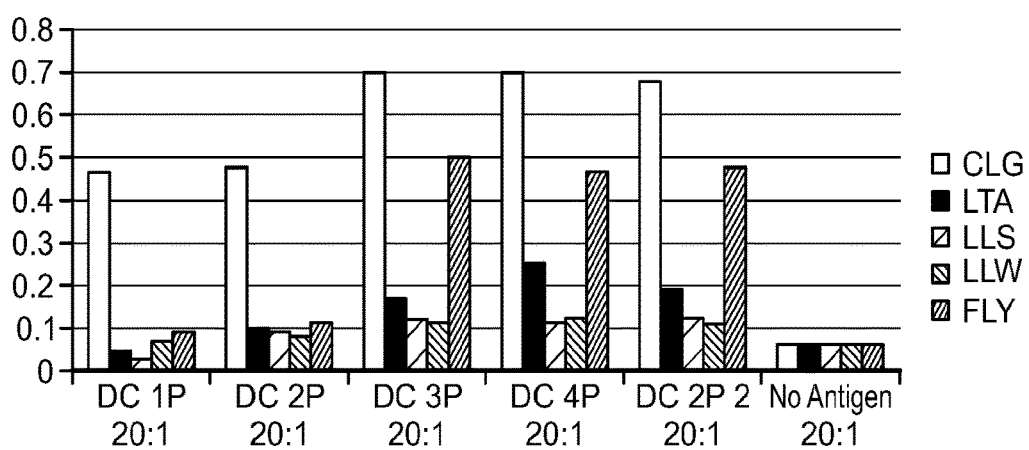
FIGS. 5, 6A, 6B, 7 and 8 show the results of a $^{51}$Cr release assay.

FIG. 5: $^{51}$Cr release at 20:1 effector:target (E/T) ratios (CTL Lines: HLA matched fibroblasts) HLA matched fibroblasts pre-pulsed with peptides from LMP2: CTL Lines established with LMP2 split on 1, 2, 3 or 4 plasmids (1P: 497 aa LMP2B; 2P: LMP2A 1$^{st}$ exon (119 aa) on 1 plasmid, LMP2A 2$^{nd}$ exon (378 aa); 3P LMP2A 1$^{st}$ exon (119 aa) on 1 plasmid, LMP2A (120-399 aa) on plasmid 2 and LMP2A (400-497 aa) on 3$^{rd}$ plasmid; 4P: LMP2A 1$^{st}$ exon (119 aa) on 1 plasmid, LMP2A (120-399 aa) on plasmid 2 LMP2A (400-440 aa) on 3rd plasmid LMP2A (440-497 aa) on 4$^{th}$ plasmid; 2P 2: Plasmid 1 (aa 120-440), Plasmid 2 (aa 440-497)

Conclusion: Splitting the LMP2 into at least two plasmids one containing aa 400 to 497, the other containing residues before 399 results in stronger responses to a greater number of subdominant epitopes EBNA-1 amino acid 90 to 325 corresponding to Gly Ala repeat domain were deleted from the EBNA-1 sequence and inserted into the p shuttle plasmid under the control of the CMV promoter. This sequence was selected for deletion because it was demonstrated to inhibit peptide processing. The following HLA-A2 restricted peptide was used to assess response: VLK 574-582 HLA A2.

Furthermore, LMP1 sequence was prepared with aa 1-43 deleted (to prevent its aggregation/protection from proteosome processing) and 260-315 deleted (5 copies of 11 amino acid tandem repeats). These sequences were constructed in the p shuttle plasmid under control of the CMV promoter and compared with wild type LMP1. To assess breadth of response, the following HLA-A2 restricted epitopes of LMP1 were prepared and tested:
YLL 125-133 YLLEMLWRL HLA A2 (SEQ ID NO:9)
YLQ 159-167 YLQQNWWTL HLA A2 (SEQ ID NO:10)
TLL 166-174 TLLVDLLWLL HLA A2 (SEQ ID NO:11)
LLV 167-175 LLVDLLWLL HLA A2 (SEQ ID NO:12)
LLL 92-100 LLLIALWNL HLA A2 (SEQ ID NO:13)
RLG 132-140 RLGATIWQL HLA A2 (SEQ ID NO:14)

Figure 6A:
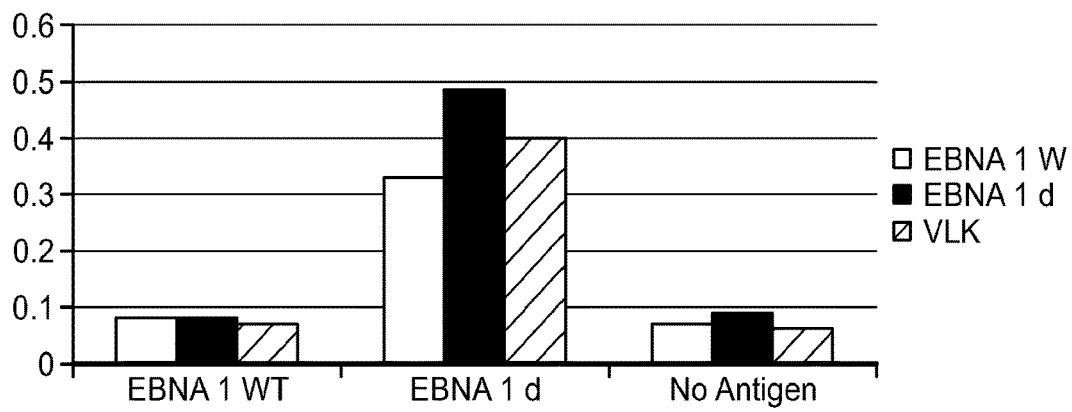
Figure 6B:
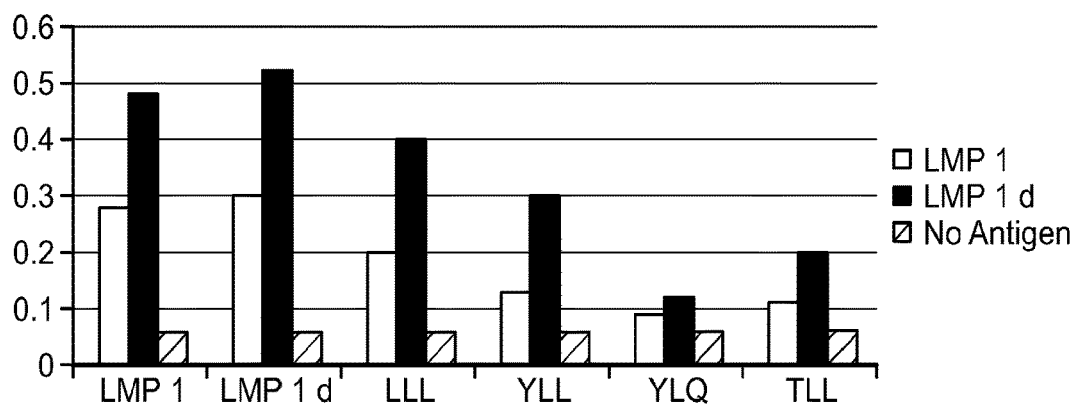

FIGS. 6A and 6B: $^{51}$Cr release at 20:1 effector:target (E/T) ratios (CTL Lines: HLA matched fibroblasts) HLA matched fibroblasts pre-pulsed with peptides from EBNA-1 or LMP1: Comparison of CTL Lines established with EBNA-1 wild type vs. EBNA-1 deleted and LMP1 wild type vs. LMP1 deleted.

Conclusion: Deletion of certain regions of proteins which evade antigen processing results in stronger responses to a greater number of subdominant epitopes b. Example 2

In the following experiments, T cells were grown in the same way as outlined in Example 1 above, with different variations designed to enhance antigen processing to favor T cells reactive with the production of subdominant epitopes.

FIG. 7: ($^{51}$Cr release) Cr release at 20:1 effector:target (E/T) ratios (CTL Lines: HLA matched fibroblasts) HLA matched fibroblasts pre-pulsed with peptides representing Dominant antigen (EBNA-3A), Subdominant antigen (LMP2) and specific HLA A2 restricted subdominant epitopes from LMP2 with CTLs made from the same patient using two different methods: one with 100 nM to 300 nM bortezomib added during antigen presentation, one without.

Figure 8:
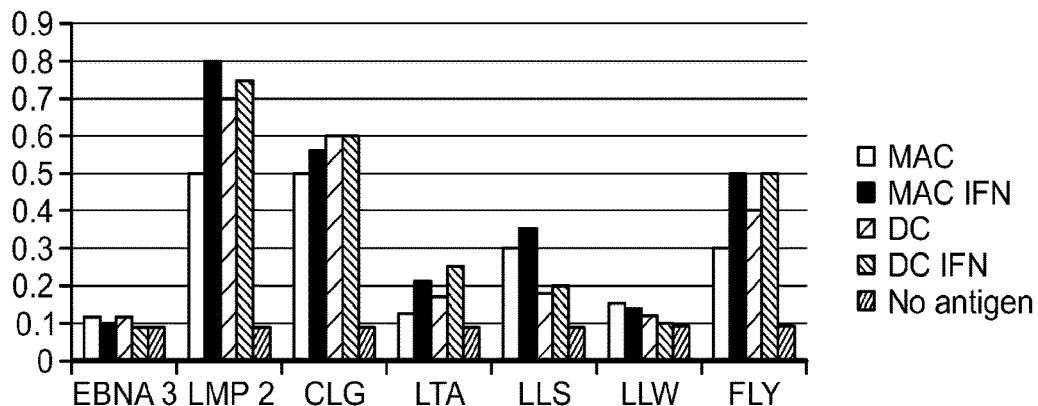

Conclusion: Addition of the Proteosome antagonist bortezomib during CTL antigen presentation modifies antigen processing to generate CTL's to a broader number of subdominant epitopes with a modest decrease in the response to dominant epitopes FIG. 8: ($^{51}$Cr release) Cr release at 20:1 effector:target (E/T) ratios (CTL Lines: HLA matched fibroblasts) HLA matched fibroblasts pre-pulsed with peptides representing Dominant antigen (EBNA-3A), Subdominant antigen (LMP2) and specific HLA A2 restricted subdominant epitopes from LMP2 with CTLs made from the same patient using two different methods: one with 10 ng/ml Interferon γ (IFNγ) added 12 hours before and during antigen presentation, one without.

Conclusion: Addition of IFNγ during CTL antigen presentation modifies antigen processing to generate CTL's to a broader number of subdominant epitopes with a modest decrease in the response to dominant epitopes. The effect is more dramatic in Macrophages than in dendritic cells.

c. Example 3: Hepatitis and Hepatocellular Carcinoma

A mouse model of chronic hepatitis has been recently developed which allows the study of the primary and secondary immune response in hepatitis B (Publicover J et al. 2011). This HBVtgRAG mouse is a cross between HBV-replication transgenic mice (HBVRpl) in the C57BL/6 background for 15 generations which constitutively allows viral replication and release of virions and RAG-1 deficient mice making them unable to generate T and B cells. When $10^8$ spleenocytes are transferred from C57BL/6 mice, the immune system is reconstituted and the primary immune response to hepatitis infection is modeled. If one administers the spleenocytes to young (3-4 week old) mice, the animals (similar to young children infected with Hepatitis B) develop chronic Hepatitis Like the humans, they clear HBc but HBs remains at high levels in the serum (FIG. 1). This model of chronic hepatitis was used in the following experiments.

Alanine aminotranferase were measured using ALT-L3K kit (Diagnostic Chemicals Ltd) on a Cobas Miras Plus analyzer (Roche diagnostics). HBs Ag was measured using ETI-MAX 2 Plus (Diasorin; HBs Antibody was measured using ETI-AB-AUK-PLUS and ABAU standard set (Diasorin). HBcAB was measured using ETI-AB-COREK-PLUS (Diasorin). Assays were read on ELx800 (Biotek Instruments) wavelength 450 nm and 630 nm.

Figure 9:
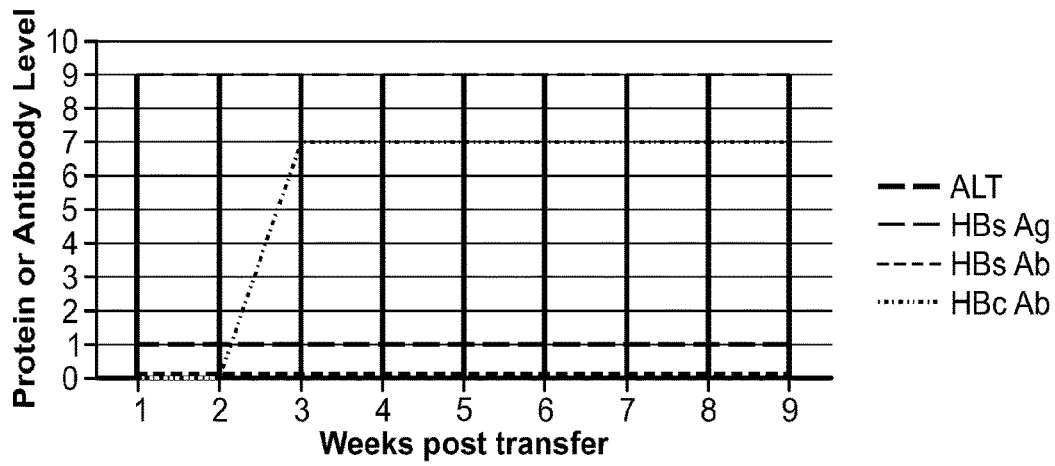
FIG. 9 shows a mouse model of chronic hepatitis B.

FIG. 9: HBVtgRAG mouse model of chronic hepatitis B.

T cells were grown to HBs ex vivo using our protocol and injected by tail vein injection 3-4 weeks post transfer of the original spleenocytes. A titration was performed from $1\times10^5$ to $1\times10^8$ cells with plateau achieved at $1\times10^6$ cells. As can be seen below, our T cell rebalancing therapy clears chronic hepatitis in the HBVtgRAG model.

Figure 10:
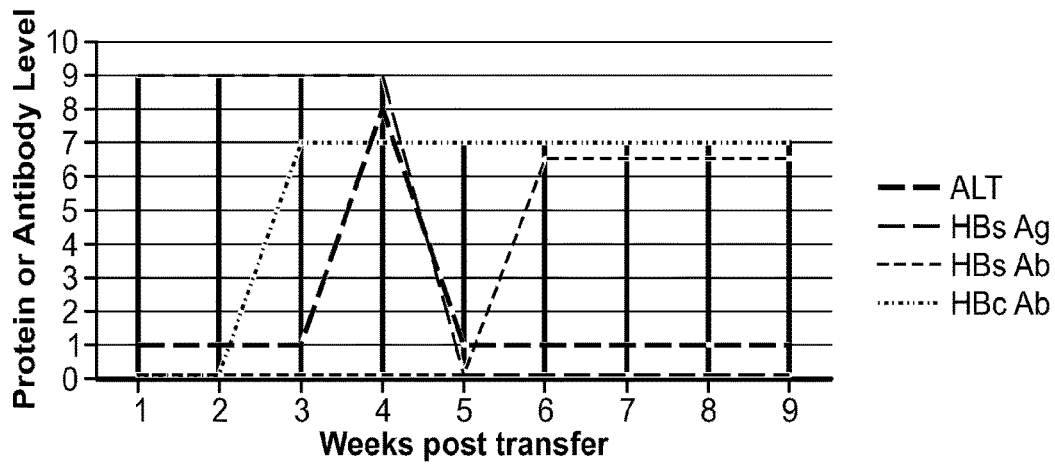
FIG. 10 shows treatment of the mouse model.

FIG. 10: Treatment of HBVtgRAG model with T cells reactive to HBs Ag lead to acute inflammation and clearance of the previously chronic infection.

When IL-4 or IL-21 were used as a supplement to the medium during antigen presentation, the amount of T cells required to achieve plateau effect was $5\times10^5$ and $7\times10^4$, respectively. This number of cells is more than a log lower than T cells expanded in the standard IL-15 protocol and indicates that polarization during culture towards T follicular helper cells and TH2 cells is advantageous. On the other hand, polarization with IL-12 increased the number of cells to $1\times10^7$ required for plateau and polarization to Treg with IL-2 and rapamycin eliminates the response to therapy.

Different Culture conditions result in polarization to different T cell subsets and different numbers of T cells to reach plateau in clearing Hepatitis in the HBVtgRAG mouse

| Culture Conditions | Number of T cells to Reach Plateau |
|---|---|
| IL-15 | $1 \times 10^6$ |
| IL-15 + IL-4 | $5 \times 10^5$ |
| IL-15 + IL-12 | $1 \times 10^7$ |
| IL-15 + IL-21 | $7 \times 10^4$ |
| IL-2 + rapamycin | No response |

Therefore, polarization of the T cells to different T cell subsets has important therapeutic effects.

Figure 11:
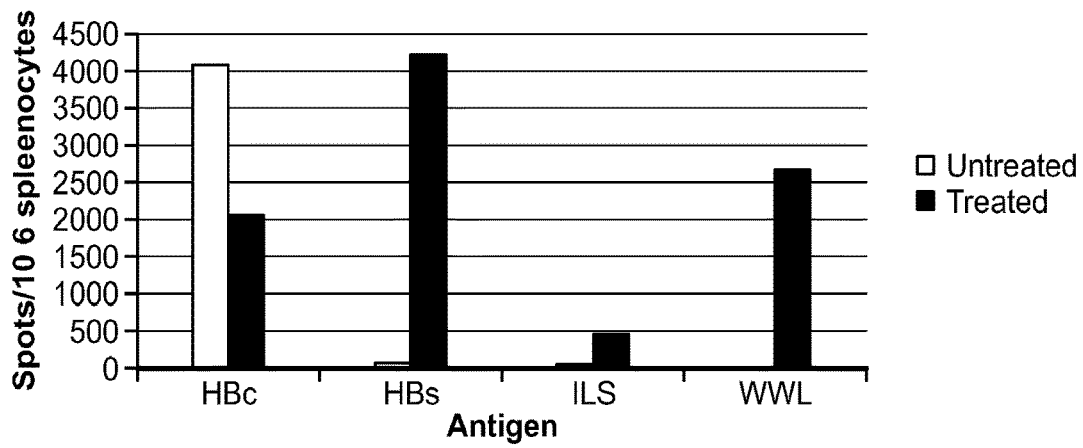
FIG. 11 shows T cell responses to HBs and HBc.

To determine the effect of T cell therapy on the frequency of T cells to different epitopes, the % of IFNγ producing epitopes to different epitopes was determined by Elispot. At week 6 post transplant, spleenocytes were collected from HBVtgRAG mice who were untreated or treated with plateau levels of T cells raised to HBs Ag. The spleenocytes were pulsed with Hepatitis Core Antigen (HBc), Hepatitis Surface Antigen (HBs) or two Kb restricted peptides of HBs: ILS or WWL.
HBs Ag 190-197 VWLSVIWM $K^b$ (SEQ ID NO:15)
HBs Ag 208-215 ILSPFLPL $K^b$ (SEQ ID NO:16)
The following results were observed:

FIG. 11: Treatment with HBs T cells rebalances the immune system to a new dominance hierarchy.

As can be seen, T cell lines produced using our protocol generated a significantly higher T cell response to HBs and a slightly decreased response to HBc. The HBs response was driven predominantly by a de novo response to a previously subdominant epitope (WWL). Thus, the dominance hierarchy within HBs was switched by T cell rebalancing therapy as the response which exists in untreated animals (albeit weak) is against the dominant epitope (ILS) switching the overall balance of the HBV response in favor of the previously subdominant HBs antigen relative to the previously dominant HBc antigen.

The HBVtgRAG mouse model was also used to investigate whether in vivo methods could also rebalance immunodominance hierarchies. In one approach, the inventors injected HBs Antigen in Freund's adjuvant by tail vein injection (IV), intramuscularly (IM) or intraperitoneally (IP). Alternatively, 100 µg plasmid DNA was administered per mouse (data not shown).

Figure 12:
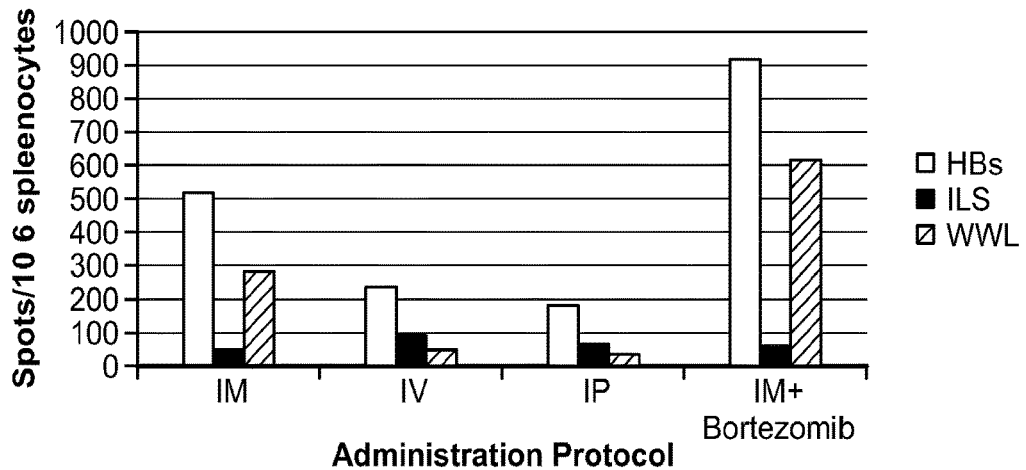
FIGS. 12 and 13 show responses by method of administration.

FIG. 12: The IM route of administration results in a broader response to subdominant antigens as dose treatment with a protease inhibitor during vaccination.

As can be seen, a 4× stronger response is generated by IM administration relative to the other two and this is associated with a response to the subdominant epitope. Furthermore, when this mouse was treated with the proteasome antagonist bortezomib, and the antigen was administered IM, the response to the subdominant epitope was further accentuated.

In a second, set of experiments the response alone and in complexes with two HBs reactive murine antibodies of different isotypes (IgG1 vs. IgG2a):
Monoclonal antibodies to HBs Ag
10-H05 Murine IgG1 HBsAg (Fitzgerald, Concord, Mass.)
10-H05A Murine IgG2a HBsAg (Fitzgerald, Concord, Mass.)

FIG. 13: IgG2a monoclonal antibody but not IgG1 antibody specific for HBs Ag results in a different dominance hierarchy and significantly better antigen presentation by the IV route.

When the antigen antibody complex was administered intravenously and IM, the IgG2a complex generated more of a response to the subdominant epitope. Further, this protocol developed a near comparable level of immune response by IV administration to that achieved by IM administration indicating that IV administration of IgG2a immune complexes may be able to rebalance the immunodominance hierarchy in vivo.

The inventors hypothesize that the likely mechanism for this observation is that IgG2a binds the high affinity FcR which is preferentially expressed on dendritic cells and thus targets the HBs antigen to dendritic cells. Additionally, as HBs Ag a determinant first loop (aa 124-147) is the major epitope for recognition by neutralizing antibodies and the ILS epitope is further away, it could be that antigen processing for ILS is enhanced.

Clinical Trial of T Cell Rebalancing Therapy in HBV Associated Hepatocellular Carcinoma 5 patients with HBV and HCC who were HLA-A *0201 were immune profiled for their Humoral and cellular immune response. Pretreatment clinical laboratory testing demonstrated high titers of antibody to hepatitis B core antigen (HBc Ag) but not to hepatitis B surface antigen (HBs Ag) (FIG. 10).

PBMC's were induced into dendritic cells, pulsed with hepatitis B core antigen (HBc Ag) and hepatitis B surface antigen (HBs Ag) and used to grow CTL's from PBMC's which were tested by Elispot for IFNγ.

Figure 14:
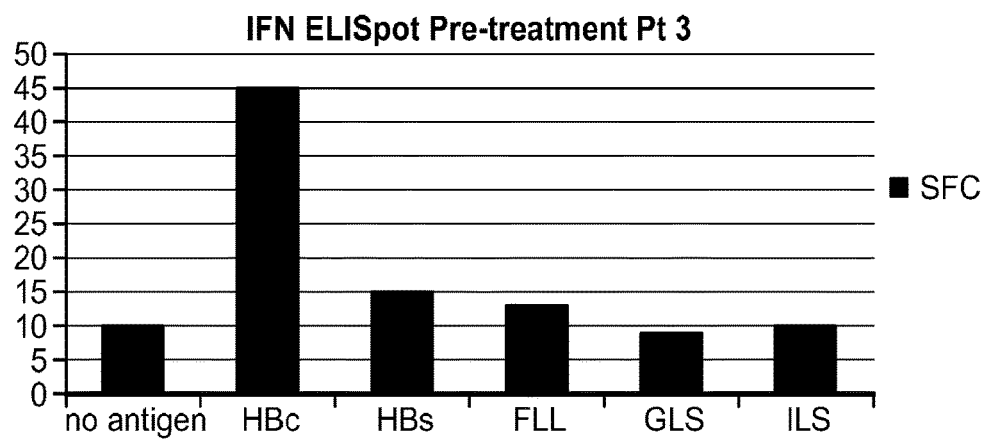
FIG. 14 shows a hierarchy of antigens.

FIG. 14: Number of Spot forming cells in $10^5$ PBMCs from Patient 3.

By frequency of IFNγ producing T cells on Elispot a hierarchy was observed: no-antigen(10 sfc)<HBsAg(15 sfc) <HBcAg(45 sfc). This indicates that Hepatitis B surface antigen is subdominant relative to Hepatitis core antigen. Additionally, 3 peptides of HBs (FLL, GLS and ILS) were studied:
HBs Ag 20-28 FLLTRILTI HLA-A*201 (SEQ ID NO:17)
HBs Ag 185-194 GLSPTVWLSV HLA-A*201 (SEQ ID NO:18)
HBs Ag 208-216 ILSPFLPLL HLA-A*201 (SEQ ID NO:19)

The FLL peptide appeared to be slightly dominant in what little response to HBs was detectable but, because of the weak response, the dominance hierarchy was confirmed by ICS assays:
Intracellular Cytokine Staining (ICS)

$5\times10^5$ CTL were resuspended and incubated for an hour in 100 µl of 1×PBS 1% FCS with peptide ($10^{-5}$ to $10^{-9}$ M final concentration) Golgi Plug (BD Biosciences, San Diego, Calif.) was then added, cells were incubated at 37 degrees C. 5% $CO_2$ for 5 hours, pelleted, washed in 200 µl PBS 1% FCS and stained for surface antigens (CD4 fluorescein isothiocyanate and CD8 allophycocyanin (Pharmingen, Becton Dickinson) 30 minutes at 4 degrees C. Following resuspension in fixation and permeabilization solution, cells were stained with anti human IFNγ phycoerythrin (Pharmingen, BD) 1/20 dilution on ice for 30 minutes, washed once and resuspended in PBS 1% FCS and analyzed on FACS Canto (Becton Dickinson)

Figure 15:
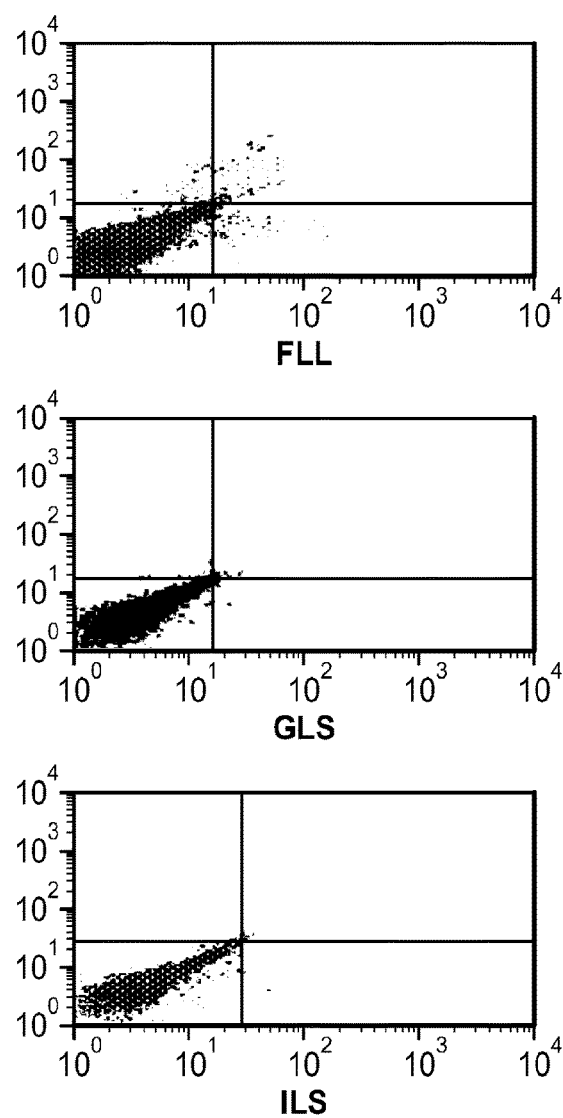
FIG. 15 shows responses by ICS.

FIG. 15: ICS Analysis of response to HBs epitopes.

Although the responses detectable by ICS weren't strong, the FLL epitope did again appear dominant relative to the other two epitopes.

$5\times10^6$ PBMC's were isolated from each patient and T cells were grown as per our protocol using HBs 15 mer peptides mixes as the stimulating antigen with the peptide with the exclusion of peptide 15-30 (to eliminate FLL). IL-4+IL-15 were used during the expansion. $1\times10^{10}$ T cells were obtained and frozen with an aliquot taken for Elispot testing.

FIG. 16: HBs Cells are the majority of the T cells which are administered to the patient and these respond to previously subdominant antigens.

As can be seen, the CTL line generated was almost exclusively reactive to the previously subdominant HBs, a response which was primarily driven by the previously subdominant epitopes. CTL's were dosed by IV Infusion at $5\times10^7$ to $1\times10^8$ cells/m$^2$ and the patients were monitored.

FIG. 17: The patient has an acute flair and then clears the hepatitis.

After developing acute hepatitis, the patient resolved and completely cleared the hepatitis. On day 14, PBMC's were again collected and a profile of the cellular immune response was re-determined.

FIG. 18: The patient's immunodominance hierarchy has been rebalanced to the previously subdominant antigen (HBs) and the previously subdominant epitopes on that antigen.

The immunodominance hierarchy has been successfully rebalanced by the T cells grown by our process. In addition to clearing the chronic hepatitis, the patient also had a complete response to his Hepatocellular carcinoma.

FIG. 19: The T cells completely resolved the patient's Hepatocellular carcinoma.

d. Example 4: Systematic Method for Treating Cancer

The clinical diagnosis and therapy of cancer involves the biopsy and imaging of the tumor to determine its tissue of origin, differentiation and extent of local and systemic metastasis. While diagnostics to genetic defects in oncogenes or tumor suppressor genes and assays to determine sensitivity to chemotherapeutic or biologic agents is sometimes performed, generally patients are treated with a combination of surgery, chemotherapy and radiation depending upon their specific cancer and stage. Similarly, while the immune system in various patients has been studied using different techniques, this information has not been used in the clinical management of the patients. With the advent of their cellular therapy to rebalance the immune system, the inventors had to establish the use of immune profiling in the management of the cancer patient. The inventors have developed a standardized immune profiling methodology which is used to select antigens which are subdominant in that patient and can be used to grow T cells in vitro which can be reinfused into the patient to rebalance the immune response to a tumor. Following therapy, the patient is reprofiled to determine if the therapy successfully rebalanced the immune response. Such a therapeutic method is novel and can result in clinical response and enhanced survival. The same approach can be used infectious diseases and autoimmunity and organ transplantation.

The first step is to identify which tumor associated antigens are present on the patient's tumor. This is generally done by immunohistochemistry on a biopsy from the patient's tumor. The panel antigens tested will depend on the type of tumor. For example, in melanoma antigens included NY-ESO-1, SSX-2, Melan A, gp100, MAGE A4, MAGE A1, Tyrosinase and would be supplemented as new tumor associated antigens were described. Not all tumors will express all of the antigens in the panel. For the antigens, which the patients tumor has, a baseline immune profile to the different antigens is determined using the systematic profiling for humoral and cellular immune response described above. Elisa is used to determine antibody titer to each antigen in the serum and the % of T cells responding to the antigen is determined by IFNγ ICS or Elispot. In this way, a base line profile is determined.

Figure 20:
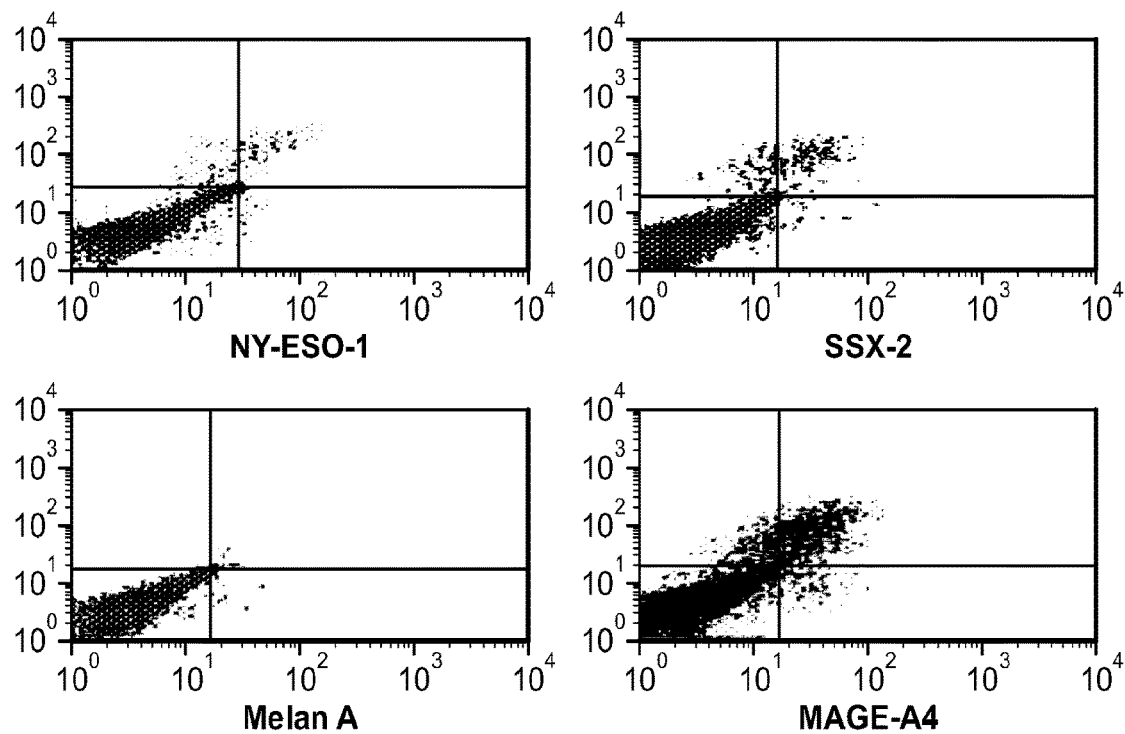
FIG. 20 shows antigens present in a patient's tumor.

FIG. 20: IFNγ ICS to a Panel of Tumor Antigens in Patient 1

In Patient 1, the patient's tumor had NYESO-1, SSX-2, Melan A, and MAGE A4. ICS demonstrated a strong response to MAGE A4 but modest/no response to NYESO-1, SSX-2 and Melan A. The NYESO-, SSX-2 and Melan A antigens are thus chosen to grow and expand CTL in the in vitro culture using the following protocol:

$5 \times 10^6$ PBMC's are isolated from the blood. Monocyte-derived dendritic cells are generated in vitro from peripheral blood mononuclear cells (PBMCs) from a patient by plating of PBMCs for 2 hours in a tissue culture flask to permit adherence of monocytes. At this point the nonadherent cells are removed and frozen at −80 to later serve as a source of T cells. Treatment of the adherent monocytes with interleukin 4 (IL-4) and granulocyte-macrophage colony stimulating factor (GM-CSF) leads to differentiation to immature dendritic cells (iDCs) in about a week. Subsequent treatment with tumor necrosis factor (TNF) further differentiates the iDCs into mature dendritic cells. These cells are then separated into 3 separate flasks (or however many antigens to which one desires to grow T cells) in RPMI 1640 media supplemented with 45% Click's medium (Irvine Scientific, Santa Ana, Calif.), 2 mM Glutamax 1 and 5% human serum. Each flask is pulsed with one of the 3 plasmids (or pepmix) containing the coding sequence for the antigen of interest (in this patient 1 containing NY-ESO-1,1 containing SSX-2 and the third containing Melan A). The cells are stored at 37 degrees C. for 2 hours. In the meantime, PBMC's are thawed and added to the pulsed dendritic cells at a 1:20 to 1:100 PBMC to Dendritic cell ratio and incubated at 37 degrees C. for 18 hours. The three flasks of cells are then pooled and resuspended in the same media, containing IL-15 (5 ng/ml) to generate in vitro expansion of the T cells which have recognized the antigen. A Grex gas permeable bioreactor is used (Wilson Wolf Manufacturing Minneapolis, Minn.) obviating the need to change media and enabling exponential growth kinetics. Generally $3 \times 10^8$ to $1.5 \times 10^{10}$ cells are obtained within 3 to 6 weeks enough cells to be administered to a patient.

T Cells Grow in Gas Permeable Bioreactor

T cells grow as a layer on the gas permeable membrane for excellent gas exchange and have a volume of media sufficient to grow to the required density.

At the end of in vitro culture, T cells are assayed in the ICS assay with the same antigens: NY-ESO-1, SSX-2, Melan A, gp100, MAGE A4, MAGE A1, Tyrosinase.

Figure 21:
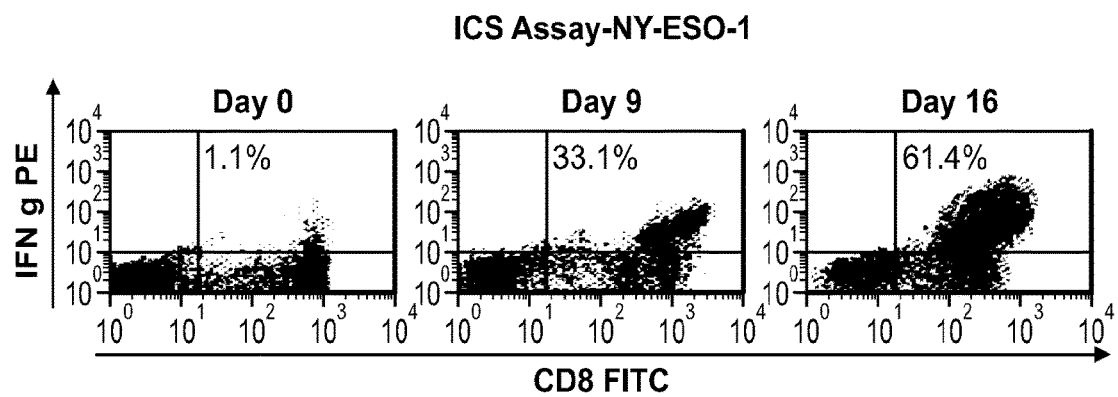
FIG. 21 shows cells responding to the NY-ESO-1 antigen.

FIG. 21: ICS Assay Patient 1

Based upon the assay, the % of the cells responding to each subdominant antigen/epitope is determined in this case, NY-ESO-1, SSX-2 and Melan A. The total number of cells responding to each subdominant antigen or epitope can be calculated using this % and the number of CTLs in the culture. In the case of patient 1, 61.4% of the cells were responding to NY-ESO-1 (FIG. 21).

Based upon this, a known dose of CTLs responsive to the subdominant antigens can be administered to the patient. CTL's were dosed at $5 \times 10^6$ to $2 \times 10^8$ cells/m$^2$.

Figure 22:
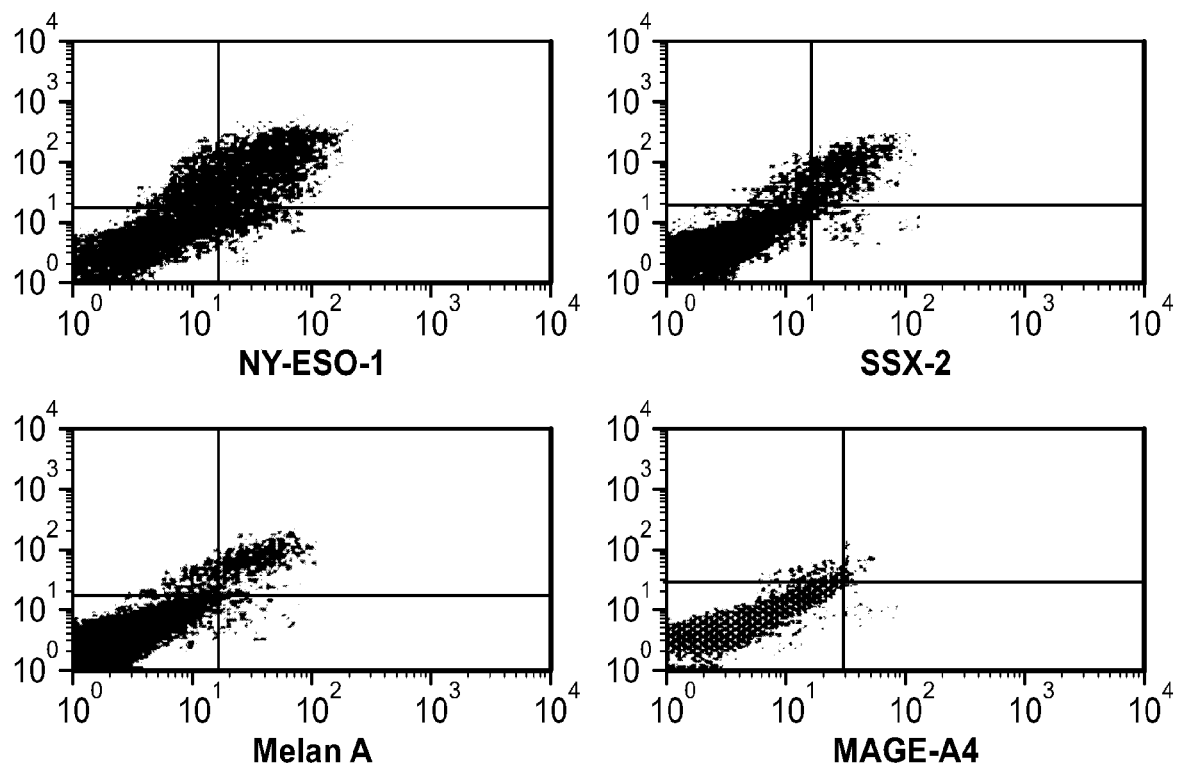
FIG. 22 shows antigens present after therapy in accordance with the present invention.

2-3 weeks after infusion into the patient, PBMC's were again collected and a profile of the cellular immune response was re-determined by ICS:

FIG. 22: Cellular Immune Profiling by ICS post therapy—Patient 1

Figure 23:
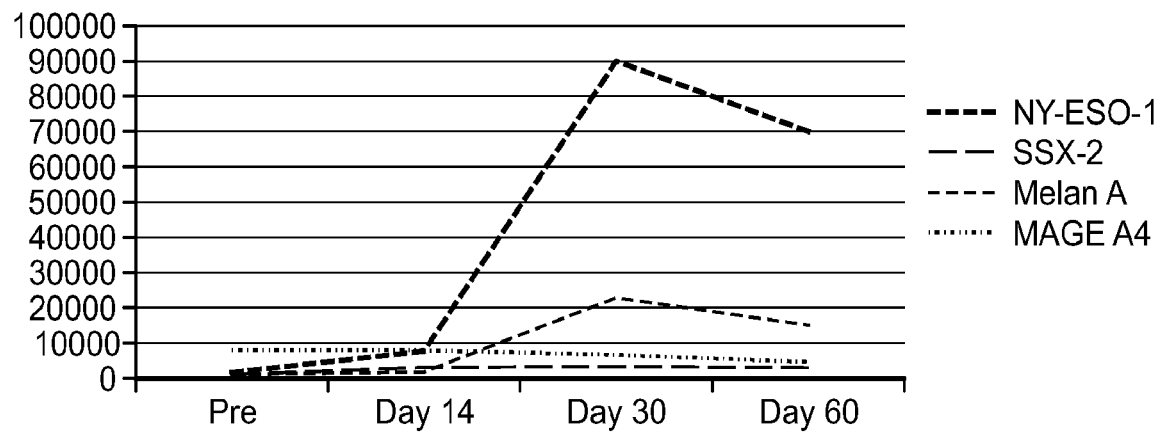
FIG. 23 shows the rebalancing of immunodominance hierarchy.

FIG. 23: Humoral Immune Profiling by ELISA—Patient 1 (Reciprocal titers of the humoral immune response are plotted below).

As can be seen from the Cellular and Humoral Profiles from the Immune Hierarchy Assays, the immunodominance hierarchy was rebalanced to favor the previously subdominant antigens.

Clinical Findings:

Clinically, the patient was a 52 year old male who was diagnosed with Stage IV metastatic melanoma. He had failed to respond to a combination regimen of Dacarbazine (DTIC) and Temodar (Temolzolomide) chemotherapy drugs in combination with IL-2.

Two years post T cell therapy, the patient is alive and has undergone a complete response. As can be seen in the Chest CT Scan the metastasis in the lung completely resolved within 6 months of Immune rebalancing Therapy and has remained stable.

Figure 24:
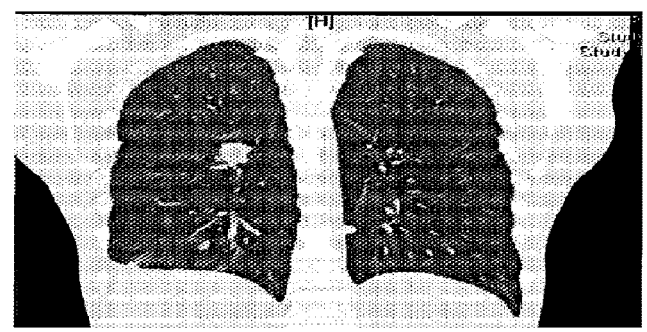
FIG. 24 is a CT scan from before and after T cell therapy in accordance with the present invention.
Figure 24:
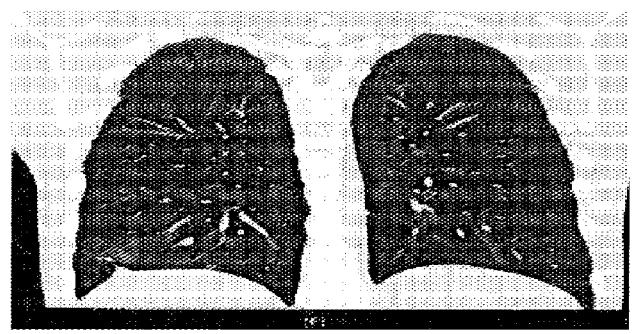

FIG. 24: CT Scan Pre and Post T Cell Therapy e. Example 5: T Cell Therapy of Lymphoma 150 adult patients with relapsed aggressive Non Hodgkins lymphoma were randomized into 3 arms: A: Rituxan+ CHOP; B: Testing for EBV LMP1 & LMP2 antigens in tumor, followed by EBV LMP1 & LMP2 T cell rebalancing and C: Pan lymphoma: No assay for antigens; Therapy with T cells grown to respond to EBV LMP1, LMP2, surviving, MAGE A3. 40% of lymphoma biopsies test positive for EBV LMP2, 50% test positive for surviving and 15% test positive for MAGE A3. Standard of Care R-CHOP regimen was used and $5 \times 10^7$ to $2 \times 10^8$ T cells were dosed per m$^2$.

Figure 25:
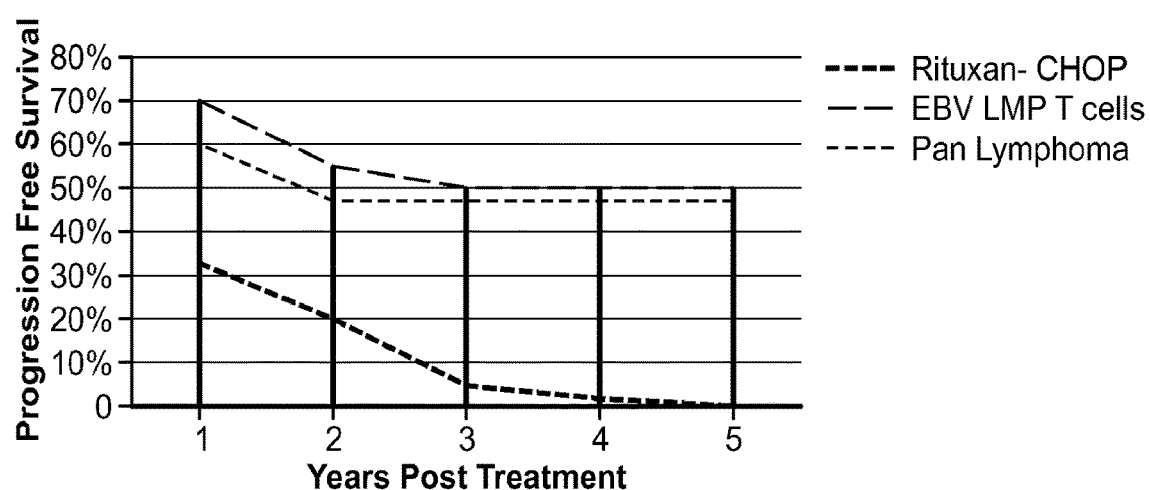
FIG. 25 shows post treatment survival, progression free.

FIG. 25: Progression Free Survival

As can be seen, T cells responsive to the tumor provide superior response rates to the current standard of care. While failures occur in year 1, post year 1 the CTL maintains patients in remission. This is evidence of a properly functioning immune system post rebalancing. Finally, while initially the EBV LMP T cells provide a better response, by year 3 the Progression Free Survival has approached that of the Pan lymphoma product. Furthermore, lymphoma today is a relapsing remitting disease with patients generally relapsing within 18 months to 2 years. CTL rebalancing therapy changes this course: once a patient's immune system is rebalanced, the patient develops a memory response which maintains a long term remission. Thus, unlike other therapies of lymphoma, T cell therapy provides a durable remission.

Figure 26:
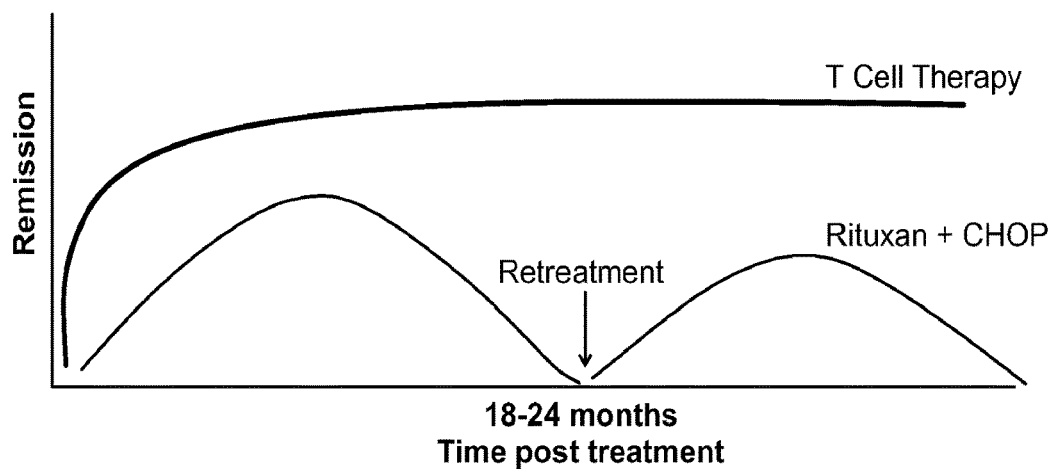
FIG. 26 shows a comparison of therapy by the present invention and Rituxan+CHOP.

FIG. 26: T Cell Therapy Changes the Natural History of Disease f. Example 6: T Cell Therapy of Autoimmune Diseases

The collagen induced arthritis model (CIA) is a model of Rheumatoid Arthritis (RA) that can be induced by immunization with heterologous collagen II (CII) in DBA/1 mice.

DBA/1 male 6-8 week old mice were obtained from Jackson Laboratories (Bar Harbor, Me.). 100 µg of bovine CII (Chondrex, Redmond, Wash.) emulsified in CFA containing 4 mg/ml *M tuberculosis* (Chondrex) were injected subcutaneously in the tail. By week 5 post injection, 80-100% of untreated mice showed fully developed disease.

T cells were grown to the following peptides using the protocols described for the in vitro growth of T cells.

Collagen Type II 263-270 immunodominant peptide used to stimulate the growth of Treg (IL-2+rapamycin)

286-300 subdominant peptide used to stimulate growth of T cells (IL-15)

Figure 27:
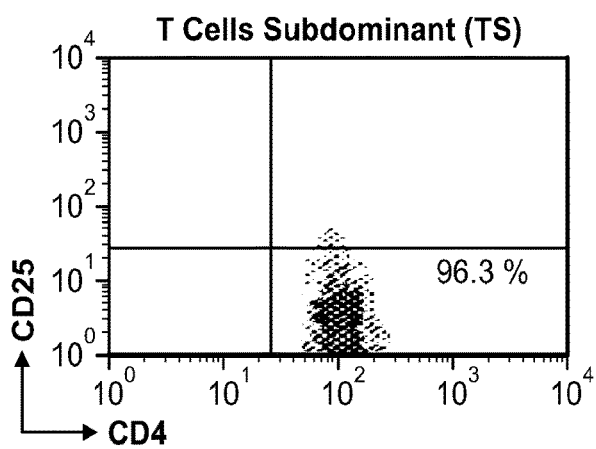
FIG. 27 shows a characterization of the T cells administered to the animals.
Figure 27:
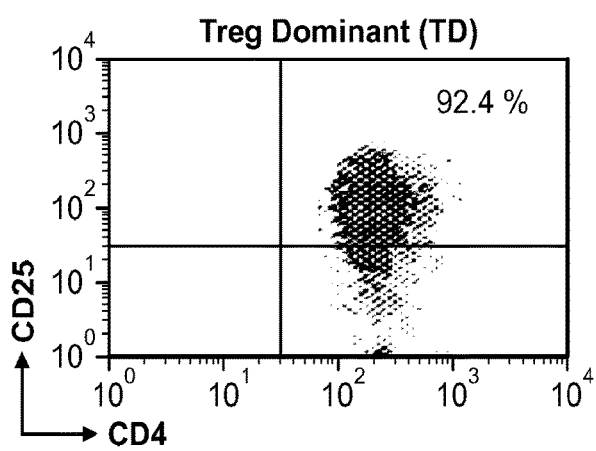
Figure 28:
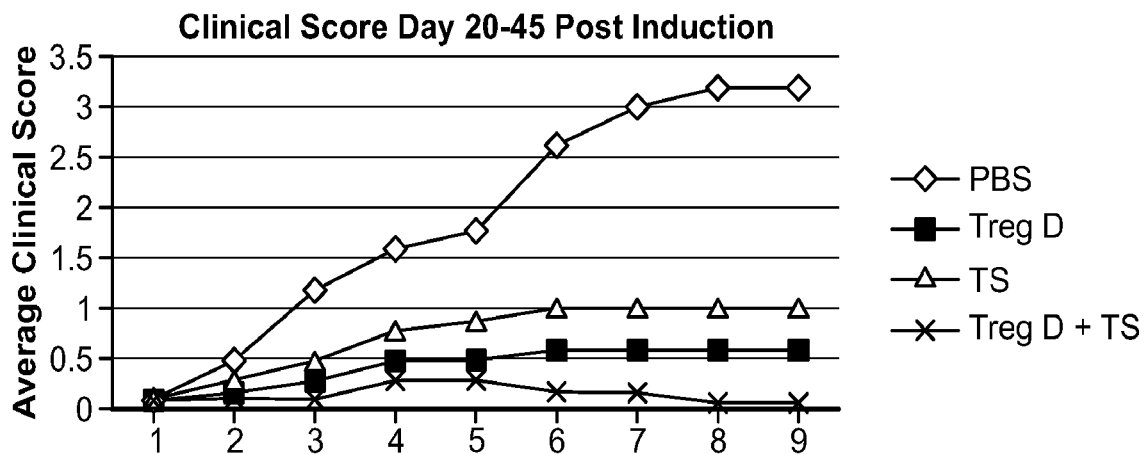
FIG. 28 shows clinical disease scores for trial mice.

5×106 cells were administered to each animal on Day 20 post induction alone or in a combination of equal parts. See FIG. 27. CD25 is a marker for Treg cells. Control animals received PBS. See FIG. 28.

Figure 29:
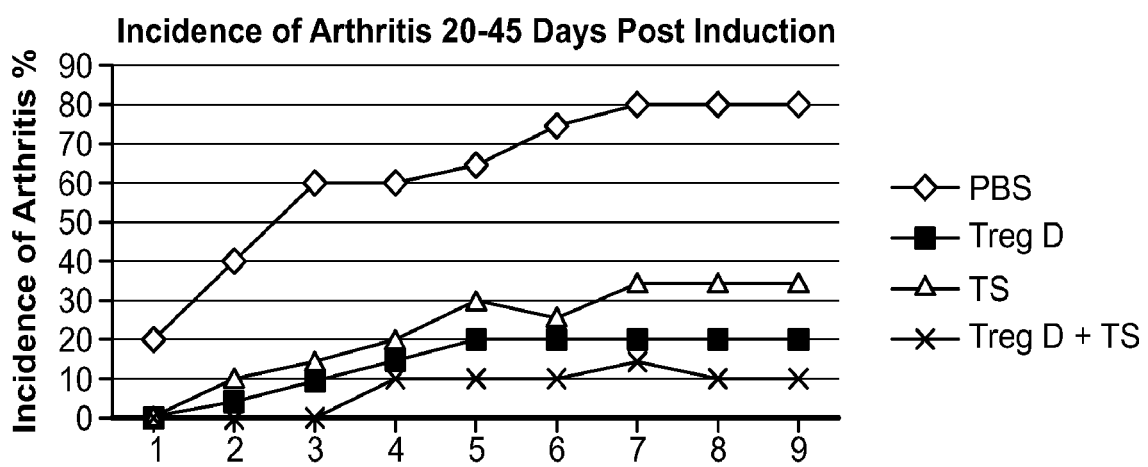
FIG. 29 shows the incidence of arthritis in trial mice.

Mice were scored for clinical disease three times per week using a score of 0-3 for each limb for a maximum total score of 12 possible: 0-1 Normal; 1 mild redness or swelling in single digits; 2 significant swelling of ankle or wrist with erythema; 3 severe swelling and erythema of multiple joints. The percent of animals with arthritic lesions in the group represent incidence of arthritis. Average clinical score in the group reflects severity of the disease. See FIG. 28 and FIG. 29.

Histopathology of Joint

Figure 30A:
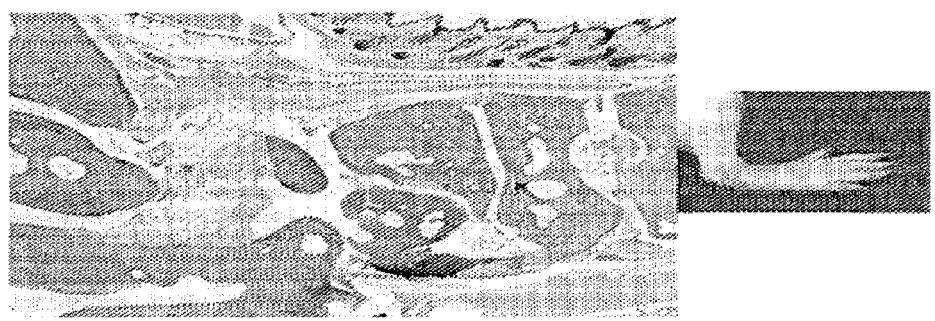
FIGS. 30A, 30B and 30C show the histopathology of a normal rat, a rat immunized with human proteoglycan and a rat treated with T cells.
Figure 30B:
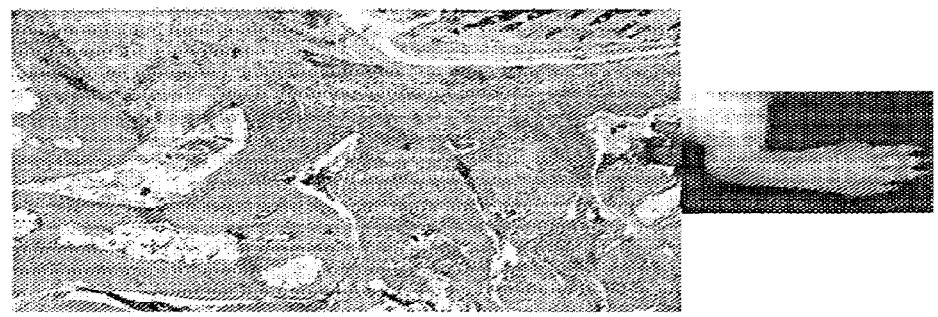
Figure 30C:
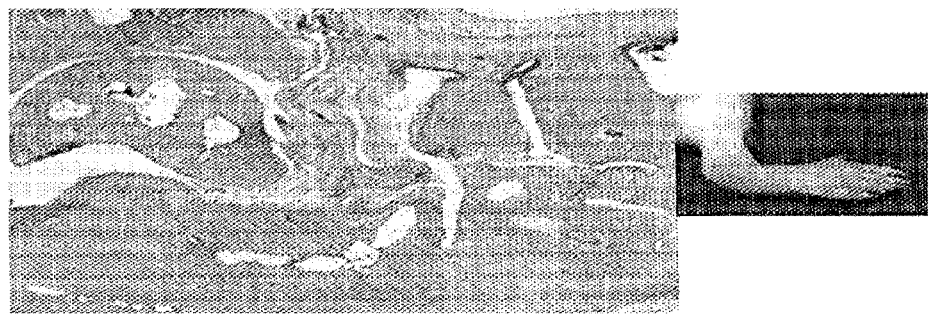

FIG. 30A shows a normal rat, FIG. 30B shows a rat immunized with human proteoglycan and FIG. 30C shows a rat treated with T cells.

As can be seen, the T cell therapy significantly decreased the incidence, severity and amount of inflammation in the joint of animals. There appeared to be a synergistic effect in rebalancing the immune response between T cells raised to subdominant epitopes and Treg grown to the dominant epitope.

What is claimed is:

1. A method for making a T cell population for use in altering the immunodominance hierarchy of a patient, comprising the steps of:

a. identifying at least one subdominant antigen or subdominant epitope in a sample obtained from the patient whose immunodominance hierarchy is to be altered, wherein the at least one subdominant antigen or subdominant epitope evokes a weaker tolerance or immune response than that of a dominant antigen or dominant epitope;
b. obtaining one or more samples from the patient, wherein the one or more samples comprise antigen presenting cells (APCs) and peripheral blood mononuclear cells (PBMCs);
c. exposing the APCs to a peptide mix derived from one or more subdominant antigens or epitopes;
d. cultivating from the PBMCs a T cell population comprising T cells capable of recognizing said subdominant antigen or epitope by
   (i) exposing the PBMCs to the APCs from step (c) in media comprising a cytokine mix consisting of IL-7 and IL-15, and lacking IL-12;
   (ii) expanding the T cells in media lacking IL-6, IL-12, and IL-27, and
   (iii) optionally restimulating the T cells by exposing to the APCs from step (c).

2. The method of claim 1, wherein the PBMCs are nonadherent.

3. The method of claim 1, further comprising a step of isolating the APCs.

4. The method of claim 1, wherein the APCs are dendritic cells.

5. The method of claim 1, wherein expanding the T cells in step (d)(ii) comprises using media comprising one or more of IL-2, IL-4, IL-7, IL 15, and IL-21.

6. The method of claim 1, wherein expanding the T cells in step (d)(ii) comprises using media comprising one or more of IL-7 and IL-15.

7. The method of claim 1, wherein the subdominant antigen or epitope comprises a viral antigen, a fungal antigen, a bacterial antigen, a parasitic antigen, a prion antigen, or a tumor antigen.

8. The method of claim 7, wherein the subdominant antigen or epitope is presented to the APCs as one or more peptides or as a plasmid or vector that expresses the subdominant antigen or epitope.

9. The method of claim 1, wherein expanding the T cells in step (d)(ii) comprises culturing the T cells in a gas permeable bioreactor.

10. The method of claim 1, wherein exposing the PBMCs to the APCs in step (d)(i) comprises exposing the PBMCs in media further comprising one or more of IL-2 and IL-4.

11. The method of claim 1, wherein expanding the T cells in step (d)(ii) comprises using media comprising one or more of IL-7, IL 15, and IL-21.

12. The method of claim 11, wherein expanding the T cells in step (d)(ii) comprises expanding the T cells in media further comprising one or more of IL-2 or IL-4.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Epstein-Barr virus

<400> SEQUENCE: 1

Leu Leu Trp Thr Leu Val Val Leu Leu
1               5

<210> SEQ ID NO 2
<211> LENGTH: 9
<212> TYPE: PRT
<213> ORGANISM: Epstein-Barr virus

<400> SEQUENCE: 2

Cys Leu Gly Gly Leu Leu Thr Met Val
1               5
```

```
<210> SEQ ID NO 3
<211> LENGTH: 9
<212> TYPE: PRT
<213> ORGANISM: Epstein-Barr virus

<400> SEQUENCE: 3

Ile Glu Asp Pro Pro Phe Asn Ser Leu
1               5

<210> SEQ ID NO 4
<211> LENGTH: 11
<212> TYPE: PRT
<213> ORGANISM: Epstein-Barr virus

<400> SEQUENCE: 4

Ser Ser Cys Ser Ser Cys Pro Leu Ser Lys Ile
1               5                   10

<210> SEQ ID NO 5
<211> LENGTH: 9
<212> TYPE: PRT
<213> ORGANISM: Epstein-Barr virus

<400> SEQUENCE: 5

Thr Tyr Gly Pro Val Phe Met Cys Leu
1               5

<210> SEQ ID NO 6
<211> LENGTH: 9
<212> TYPE: PRT
<213> ORGANISM: Epstein-Barr virus

<400> SEQUENCE: 6

Leu Leu Ser Ala Trp Ile Leu Thr Ala
1               5

<210> SEQ ID NO 7
<211> LENGTH: 9
<212> TYPE: PRT
<213> ORGANISM: Epstein-Barr virus

<400> SEQUENCE: 7

Leu Thr Ala Gly Phe Leu Ile Phe Leu
1               5

<210> SEQ ID NO 8
<211> LENGTH: 8
<212> TYPE: PRT
<213> ORGANISM: Epstein-Barr virus

<400> SEQUENCE: 8

Phe Leu Tyr Ala Leu Ala Leu Leu
1               5

<210> SEQ ID NO 9
<211> LENGTH: 9
<212> TYPE: PRT
<213> ORGANISM: Epstein-Barr virus

<400> SEQUENCE: 9

Tyr Leu Leu Glu Met Leu Trp Arg Leu
1               5

<210> SEQ ID NO 10
```

```
<211> LENGTH: 9
<212> TYPE: PRT
<213> ORGANISM: Epstein-Barr virus

<400> SEQUENCE: 10

Tyr Leu Gln Gln Asn Trp Trp Thr Leu
1               5

<210> SEQ ID NO 11
<211> LENGTH: 10
<212> TYPE: PRT
<213> ORGANISM: Epstein-Barr virus

<400> SEQUENCE: 11

Thr Leu Leu Val Asp Leu Leu Trp Leu Leu
1               5                   10

<210> SEQ ID NO 12
<211> LENGTH: 9
<212> TYPE: PRT
<213> ORGANISM: Epstein-Barr virus

<400> SEQUENCE: 12

Leu Leu Val Asp Leu Leu Trp Leu Leu
1               5

<210> SEQ ID NO 13
<211> LENGTH: 9
<212> TYPE: PRT
<213> ORGANISM: Epstein-Barr virus

<400> SEQUENCE: 13

Leu Leu Leu Ile Ala Leu Trp Asn Leu
1               5

<210> SEQ ID NO 14
<211> LENGTH: 9
<212> TYPE: PRT
<213> ORGANISM: Epstein-Barr virus

<400> SEQUENCE: 14

Arg Leu Gly Ala Thr Ile Trp Gln Leu
1               5

<210> SEQ ID NO 15
<211> LENGTH: 8
<212> TYPE: PRT
<213> ORGANISM: Hepatitis B virus

<400> SEQUENCE: 15

Val Trp Leu Ser Val Ile Trp Met
1               5

<210> SEQ ID NO 16
<211> LENGTH: 8
<212> TYPE: PRT
<213> ORGANISM: Hepatitis B virus

<400> SEQUENCE: 16

Ile Leu Ser Pro Phe Leu Pro Leu
1               5

<210> SEQ ID NO 17
<211> LENGTH: 9
<212> TYPE: PRT
```

-continued

```
<213> ORGANISM: Hepatitis B virus

<400> SEQUENCE: 17

Phe Leu Leu Thr Arg Ile Leu Thr Ile
1               5

<210> SEQ ID NO 18
<211> LENGTH: 10
<212> TYPE: PRT
<213> ORGANISM: Hepatitis B virus

<400> SEQUENCE: 18

Gly Leu Ser Pro Thr Val Trp Leu Ser Val
1               5                   10

<210> SEQ ID NO 19
<211> LENGTH: 9
<212> TYPE: PRT
<213> ORGANISM: Hepatitis B virus

<400> SEQUENCE: 19

Ile Leu Ser Pro Phe Leu Pro Leu Leu
1               5
```